(12) United States Patent
Eickhoff et al.

(10) Patent No.: US 8,889,723 B2
(45) Date of Patent: Nov. 18, 2014

(54) AMINOALKYLOXAZOLE AND AMINOALKYLTHIAZOLECARBOXYLIC ACID AMIDES AS REGENERATION-PROMOTING SUBSTANCES FOR SENSORY ORGANS AND POST-MITOTIC TISSUES

(71) Applicant: EMC microcollections GmbH, Tubingen (DE)

(72) Inventors: Holger Eickhoff, Herrenberg (DE); Hubert Lowenheim, Tubingen (DE)

(73) Assignee: EMC microcollections GmbH (DE)

( * ) Notice: Subject to any disclaimer, the term of this patent is extended or adjusted under 35 U.S.C. 154(b) by 0 days.

(21) Appl. No.: 14/208,419

(22) Filed: Mar. 13, 2014

(65) Prior Publication Data

US 2014/0288135 A1    Sep. 25, 2014

Related U.S. Application Data

(62) Division of application No. 13/577,503, filed as application No. PCT/EP2011/000502 on Feb. 4, 2011, now abandoned.

(30) Foreign Application Priority Data

Feb. 8, 2010  (DE) .......................... 10 2010 007 281

(51) Int. Cl.
*A61K 31/422*   (2006.01)
*C07D 263/30*   (2006.01)
*C07D 413/06*   (2006.01)

(52) U.S. Cl.
CPC .................................. *C07D 413/06* (2013.01)
USPC .......................................... 514/374; 548/236

(58) Field of Classification Search
USPC .......................................... 514/374; 548/236
See application file for complete search history.

(56) References Cited

U.S. PATENT DOCUMENTS

| 5,378,803 A | 1/1995 | Morgan et al. |
| 2003/0069292 A1 | 4/2003 | Hogenkamp et al. |
| 2007/0244117 A1 | 10/2007 | Fensholdt et al. |

FOREIGN PATENT DOCUMENTS

| CN | 1353605 | 6/2002 |
| CN | 1906155 | 1/2007 |
| EP | 2 009 005 A1 | 12/2008 |
| WO | 00/18407 A1 | 4/2000 |
| WO | 02/04605 A2 | 1/2002 |
| WO | 99/42088 A2 | 8/2009 |

OTHER PUBLICATIONS

H. Löwenheim et al., "Regenerative Medizin in der Therapie der Innenohrschwerhörigheit," HNO, vol. 56, No. 3, Feb. 22, 2008, pp. 288-300.
S. Chen et al., "Dedifferentiation of lineage-committed cells by a small molecule," J Am Chem Soc 126(2), Jan. 21, 2004, pp. 410-411 (Abstract only).
J.T. Corwin et al., "Regeneration of sensory hair cells after acoustic trauma," Science 240, Jun. 24, 1988, pp. 1772-1774 (Abstract only).
D.A. Cotanche, "Regeneration of hair cell stereociliary bundles in the chick cochlea following severe acoustic trauma," Hear Res 30(2-3), 1987, pp. 181-196 (Abstract only).
D.A. Cotanche, "Structural recovery from sound and aminoglycoside damage in the avian cochlea," Audio Neurootol 4(6), Nov.-Dec. 1999, pp. 271-285 (Abstract only).
R.M. Cruz et al., "Light microscopic evidence of hair cell regeneration after gentamicin toxicity in chick cochlea," Arch Otolaryngol Head Neck Surg 113(10), Oct. 1987, pp. 1058-1062 (Abstract only).
N. Daudet et al., "Characterization of atypical cells in the juvenile rat organ of corti after aminoglycoside ototoxicity," J Comp Neurol 401, 1998, pp. 145-162 (Abstract only).
N. Daudet et al., "Transforming growth factor-alpha-induced cellular changes in organotypic cultures of juvenile, amikacin-treated rat organ of corti," J Comp Neuro! 442(1), Jan. 1, 2002, pp. 6-22 (Abstract only).
B. Feng et al., "Molecules that promote or enhance reprogramming of somatic cells to induced pluripotent stem cells," Cell Stem Cell 4(4), Apr. 3, 2009, pp. 301-312 (Abstract only).
H. Hahn et al., "Whole organ culture of the postnatal sensory inner ear in simulated microgravity," J Neurosci Meth 171(1), Jun. 15, 2008, pp. 60-71 (Abstract only).
M. Izumikawa et al., "Auditory hair cell replacement and hearing improvement by Atoh1 gene therapy in deaf mammals," Nat Med 11(3), Mar. 2005, pp. 271-276 (Abstract only).
Kohei Kawamoto et al., "*Math1* Gene Transfer Generates New Cochlear Hair Cells in Mature Guinea Pigs in Vivo," J Neurosci 23(11), Jun. 1, 2003, pp. 4395-4400.
Matthew W. Kelley et al., "Replacement of Hair Cells after Laser Microbeam Irradiation in Cultured Organs of Corti from Embryonic and Neonatal Mice," J Neurosci 15(4), Apr. 1995, pp. 3013-3026.
Sungwoo Kim et al., "Dedifferentiation? What's next?" Mol Interv 4(2), Apr. 2004, pp. 83-85.
H. Li et al., "Pluripotent stem cells from the adult mouse inner ear," Nat Med 9(10), Oct. 2003, pp. 1293-1299 (Abstract only).

(Continued)

*Primary Examiner* — Samantha Shterengarts
(74) *Attorney, Agent, or Firm* — DLA Piper LLP (US)

(57) ABSTRACT

A method of treating inner ear hardness of hearing and restoring hearing of humans and animals after damage and loss of sensory hair cells in an organ of Corti based on regeneration biology includes administering a therapeutically effective amount of a compound including aminoalkyloxazole and aminoalkylthiazole carboxylic acid amides, or a pharmaceutically acceptable salt, a stereoisomer, a stereoisomer mixture, a tautomer or a prodrug compound thereof, directly or indirectly to damaged tissue structures in a cochlea, optionally, by transtympanal injection into a middle ear, by application to a round or oval window of an inner ear or by injection into the inner ear.

10 Claims, 10 Drawing Sheets

(56) References Cited

OTHER PUBLICATIONS

W. Li et al., "Small molecules that modulate embryonic stem cell fate and somatic cell reprogramming," Trends Pharmacol Sci 31(1), Jan. 2010, pp. 36-45 (Abstract only).
R. Martinez-Monedero et al., "Stem cells for the replacement of inner ear neurons and hair cells," Int J Dev Biol 51(6-7), 2007, pp. 655-661 (Abstract only).
R. Martinez-Monedero et al., "The potential role of endogenous stem cells in regeneration of the inner ear," Hear Res 227(1-2), May 2007, pp. 48-52 (Abstract only).
Christopher J. McGann et al., "Mammalian myotube dedifferentiation induced by newt regeneration extract," Proc Natl Acad Sci 98(24), Nov. 20, 2001, pp. 13699-13704.
Y Naito et al., "Transplantation of bone marrow stromal cells into the cochlea of chinchillas," Neuroreport 15(1), Jan. 19, 2004, pp. 1-4 (Abstract only).
S.J. Odelberg, "Inducing cellular dedifferentiation: a potential method for enhancing endogenous regeneration in mammal," Semin Cell Dev Biol 13(5), Oct. 2002, pp. 335-343 (Abstract only).
K. Oshima et al., "Differential distribution of stem cells in the auditory and vestibular organs of the inner ear," J Assoc Res Otolaryngol 8(1), Mar. 2007, pp. 18-31 (Abstract only).
D.W. Roberson et al., "Cell division in the gerbil cochlea after acoustic trauma," Am J Otol 15(1), Jan. 1994, pp. 28-34 (Abstract only).
Brenda M. Ryals et al., "Hair Cell Regeneration after Acoustic Trauma in Adult Coturnix Quail," Science 240(4860), Jun. 24, 1988, pp. 1774-1776.
R.C. Schugar et al., "Small molecules in stem cell self-renewal and differentiation," Gene Ther 15 (2), Jan. 2008, pp. 126-135 (Abstract only).
Pascal Senn et al., "Robust Postmortem Survival of Murine Vestibular and Cochlear Stem Cells," J Assoc Res Otolaryngol 8(2),, Jun. 2007, pp. 194-204.
J.W. Smolders, "Functional recovery in the avian ear after hair cell regeneration," Audiol Neurootol 4(6), Nov.-Dec. 1999, pp. 286-302 (Abstract only).
M. Stanchev et al., "Synthesis and antimicrobial activity in vitro of new amino acids and peptides containing thiazole and oxazole moieties," Arch Pharm 332(9), Sep. 1999, pp. 297-304 (Abstract only).
I.G. Stankova et al., "Synthesis of thiazole, imidazole and oxazole containing amino acids for peptide backbone modification," J Peptide Sci 5(9), Sep. 1999, pp. 392-398 (Abstract only).
K. Takahashi et al., "Induction of pluripotent stem cells from mouse embryonic and adult fibroblast cultures by defined factors," Cell 126(4), Aug. 25, 2006, pp. 663-676 (Abstract only).
I. Tateya et al., "Fate of neural stem cells grafted into injured inner ears of mice," Neuroreport 14(13), Sep. 15, 2003, pp. 1677-1681 (Abstract only).
P.A. Tsonis, "Regeneration in vertebrates," Dev Biol 221(2), May 15, 2000, pp. 273-284 (Abstract only).
P.A. Tsonis, "Regenerative biology: the emerging field of tissue repair and restoration," Differentiation 70(8), Oct. 2002, pp. 397-409 (Abstract only).
P. Vago et al., "Amikacin intoxication induces apoptosis and cell proliferation in rat organ of Corti," Neuroreport 9(3), Feb. 16, 1998, pp. 431-436 (Abstract only).
P.M. White et al., "Mammalian cochlear supporting cells can divide and trans-differentiate into hair cells," Nature 441(7096), Jun. 22, 2006, pp. 984-987 (Abstract only).
Y. Xu et al., "A chemical approach to stem-cell biology and regenerative medicine," Nature 453(7193), May 2008, pp. 338-344 (Abstract only).
T. Yamasoba et al., "Changes in cell proliferation in rat and guinea pig cochlea after aminoglycoside-induced damage," Neurosci Lett 347(3), Aug. 28, 2003, pp. 171-174 (Abstract only).
Tatsuya Yamasoba et al., "Supporting cell proliferation after hair cell injury in mature guinea pig cochlea in vivo," Cell Tissue Res 325, 2006, pp. 23-31.
Ifo-Institut für Wirtschaftsforschung in cooperation with Infratest Gesundheitsforschung on behalf of the German Green Cross, Marbug "Hörtest 1985," Section "Gutes Hören," 1986 (1 sheet of partial English translation). Equivalent to "Gesundheitsberichterstattung des Bundes-Heft 29," listed below.
M. Streppel et al., "Gesundheitsberichterstattung des Bundes-Heft 29," Robert Koch-Institute Study, 2006, 1 sheet of partial English translation, 2 cover sheets and pp. 3-43.
D. Kaiser et al., "X-Ray Structures and ab initio Study of he Conformational Properties of Novel Oxazole and Thiazole Containing di- and Tripeptide Mimetics," J. Chem. Soc. Perkin Trans., 2000, vol. 2, pp. 1081-1085.
Nadol, J.B., Jr., "Hearing Loss," The New England Journal of Medicine, 1993, pp. 1092-1102.
Ruben, R.J., "Development of the Inner Ear of the Mouse," Acta Oto Laryng, 1967, vol. 220, pp. 1-44.
Staecker, H., "Technical Comments: Regeneration and Mammalian Auditory Hair Cells," Science, 1995, vol. 267, vol. 709-711.
Tsonis, P.A., "Stem Cells from Differentiated Cells," Molecular Interventions, 2004, vol. 4, issue 2, pp. 81-83.
G. Videnov et al., "Synthesis of Naturally Occurring, Conformationally Restricted Oxazole- and Thiazole Containing Di- and Tripeptide Mimetics," Angew. Chem. Int. Ed. Engl., vol. 35, Nos. 13/14, pp. 1503-1506.
Nobuyuki Ito, Cancer Science 94(1), (2003) 3-8.
Database Registry Chemical Abstracts Service, Columbus, Ohio, Accession No. RN 1240216-68-5, Entered STN: Sep. 8, 2010.
Database Registry Chemical Abstracts Service, Columbus, Ohio, Accession No. RN 1023141-85-6, Entered STN: May 28, 2008.
English translation of the Chinese Official Action dated Mar. 10, 2014 from corresponding Chinese Patent Application No. 201180017156.5.

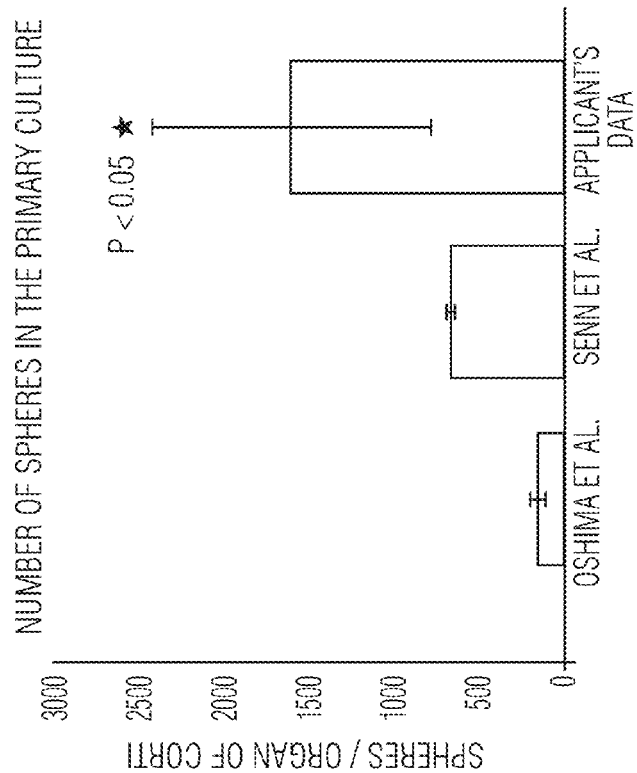
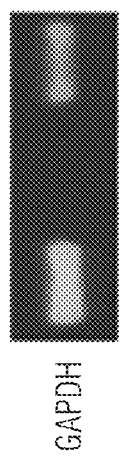
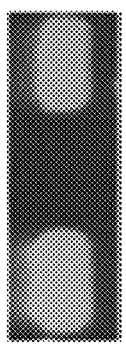
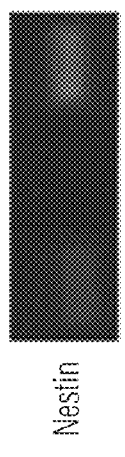
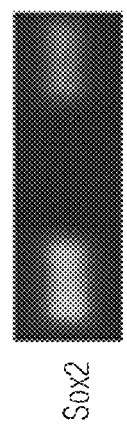
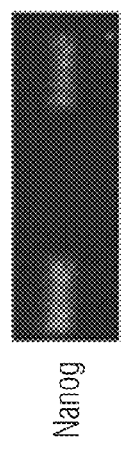
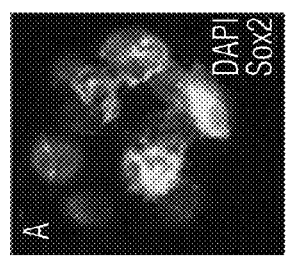
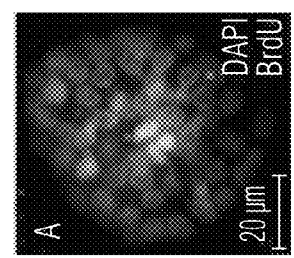

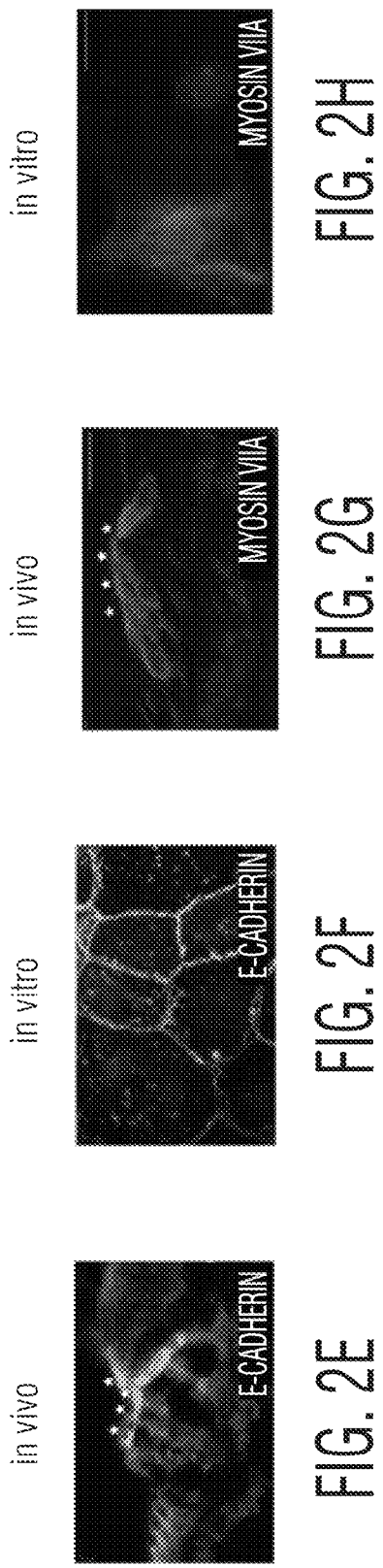

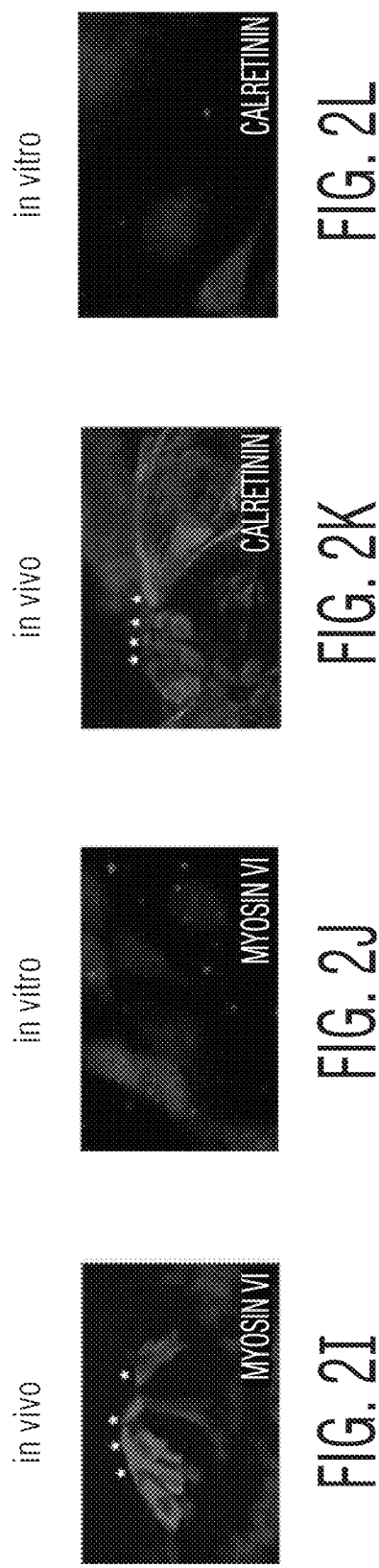

AMINOALKYLOXAZOLE AND AMINOALKYLTHIAZOLECARBOXYLIC ACID AMIDES AS REGENERATION-PROMOTING SUBSTANCES FOR SENSORY ORGANS AND POST-MITOTIC TISSUES

TECHNICAL FIELD

This disclosure relates to aminoalkyloxazole and aminoalkylthiazolecarboxylic acid amides that stimulate endogenous regeneration of terminally differentiated cells in highly specialized organs, tissues and sensory epithelia in mammals in situ.

The disclosure in particular relates to compounds with which a de novo formation of hair sensory cells in the organ of Corti can be obtained by inducing cell separation of supportive cells of the inner ear and hearing can be restored after hair cell loss.

The disclosure further relates to processes for preparing formulations of our compounds as pharmaceutical preparations and use thereof for producing pharmaceuticals for regenerative medicine.

BACKGROUND

In virtually all professional and social spheres, impaired hearing and thus a restricted ability to communicate have considerable implications on the quality of life. The sensory disorder "hardness of hearing" is one of the most urgent health problems in a society depending on communication.

On average, hardness of hearing affects about 10% of the population of the industrialized nations. In Germany, there are estimated to be 16 million people who are hard of hearing, almost one fifth of the total population (ifo-Institut, 1986). Thus, hardness of hearing is not only the most frequent disorder of a sensory organ, but also one of the most frequent chronic disorders in general.

Looking at the causes of hardness of hearing, in about 80% of the cases, the people affected suffer from sensorineural hearing loss. One of the most frequent reasons for this is the loss of sensory hair cells in the organ of Corti, the auditory sensory epithelium which, due to exposure to noise, side-effects of ototoxic medicaments, age-related degeneration or genetic causes are lost irreversibly by cell death (Nadol, 1993).

Hitherto, only the prosthetic provision of hearing aids can be offered for this most frequent form of hearing loss. However, for the persons affected, the result of this provision is often unsatisfactory due to the lack of speech recognition. Accordingly, hearing aids are actually used by only a relatively small proportion of the hard of hearing.

To date, there is no curative medical treatment option for the main cause of sensorineural hearing loss. Such a causal treatment would be possible only by replacing or regenerating the lost sensory hair cells of the organ of Corti.

In most mammalian organs and tissues, the ability for regeneration after damage is limited, or not present at all. Only very few organs and tissues such as, for example, liver, bones or skin have, over the entire lifetime of the organism, the ability for spontaneous regeneration by forming new cells. In many cases, the corresponding cells in the highly specialized organs and tissues (for example, heart, brain, skeletal muscle or the sensory epithelia of eye and inner ear) leave the cell cycle irreversibly to remain in a terminally differentiated state. As a consequence, these tissues also lose their ability to spontaneously regenerate in the case of damaging events. Accordingly, this leads to irreversible functional deficits. Thus, for example, a myocardial infarct in the case of the heart or a stroke in the case of the brain often means irreversible damage of the tissue areas affected, with corresponding permanent loss of function.

There are, however, for example, in amphibians, tissues and organs, exemplified by retina and extremities, where there is terminal differentiation, but which are nevertheless capable of spontaneous in vivo regeneration (Tsonis, 2000; Tsonis, 2002). The central cell biological event in these examples is cellular dedifferentiation, which allows generation of multipotent precursor cells from which regenerated cells may be formed by proliferation and redifferentiation.

Thus, dedifferentiation plays the decisive role in regeneration of terminally differentiated tissue of amphibious animals. In contrast, other vertebrates have low regeneration abilities.

Until about 20 years ago, for the hearing organ of mammals and birds, it was assumed that the sensory hair cells in the inner ear can be formed only during a short critical phase of embryonic development (Ruben, 1967). After this phase, the sensory epithelia were thought to be postmitotic and therefore not able to regenerate their sensory cells. However, surprisingly it was discovered that, after acoustic trauma and ototoxic damage, avian cochlea are capable of spontaneously regenerating sensory hair cells (Cotanche 1987; Cruz et al., 1987).

Cell division of supportive cells directly adjacent to the destroyed sensory hair cells has been described as the basic biological mechanism for sensory hair cell regeneration in avian cochlea (Corwin and Cotanche, 1988; Ryals and Rubel, 1988), where a population of undifferentiated cells is formed which are capable of redifferentiation to newly formed sensory hair cells and supportive cells. The result is the virtually complete morphological and functional recovery of the sensory epithelium in birds (Cotanche, 1999; Smolders, 1999).

Although this was initially obvious, due to fundamental cell biological differences, it has hitherto not been possible to apply findings from other models to mammals.

Corresponding experiments concerning regeneration of sensory hair cells in mammals gave no (Roberson and Rubel, 1994; Vago et al., 1998; Daudet et al., 1998; Daudet et al., 2002; Yamasoba et al., 2003) or very few (Yamasoba and Kondo, 2006) indications of a capability for spontaneous cell division of supportive cells in the organ of Corti. In particular, even after administration of growth factors, there are no indications of an inducible proliferation of supportive cells in the organ of Corti (Staecker et al., 1995; Daudet et al., 2002). Various experiments with cultures of early development stages of the organ of Corti of embryonal mice likewise showed, after defined laser damage, only individual proliferative events (Kelley et al., 1995).

This total lack of cell divisions suggests that the highly specialized supportive cell populations in the normal adult organ of Corti have reached a terminally differentiated state and are unable to re-enter the cell cycle. Thus, in the case of the inner ear, even a single acoustic trauma may result in the destruction of sensory hair cells, followed by unavoidable and irreversible loss of hearing.

It had recently been found that an extract can be obtained from amphibian tissues (for example, extremities) undergoing regeneration which is capable of inducing dedifferentiation even in mammalian cells (McGann et al., 2001). Using this extract, with appropriate stimulation, the dedifferentiation-based mechanism for regeneration of terminally differentiated cells can be transferred from amphibians to mammals (Odelberg, 2002). However, regeneration extracts mentioned are "protein cocktails" and details with regard to their composition are not known.

However, in the meantime, it has also been possible to achieve a corresponding effect in mammalian muscle cells using a defined low-molecular-weight compound (Chen et al., 2004). By screening, is was furthermore possible to identify several low-molecular-weight compounds producing regeneration biology-relevant effects in various cell types including glia cells (reviews in Xu et al., 2008; Schugar et al., 2008; Feng et al., 2009; Li and Ding, 2009). These effects suggest that it may also be possible to induce dedifferentiation-based regeneration in further cell types using suitable low-molecular-weight compounds (Tsonis, 2004; Kim et al., 2004; Odelberg, 2002).

Hitherto, the transfer of this concept to regeneration biological studies on the inner ear has been unique. Low-molecular-weight compounds capable of effecting sensory hair cell regeneration in the inner ear are neither known nor patented.

As yet, other concepts pursued in the current art for regenerating sensory hair cells in the organ of Corti likewise show little promise with regard to clinical application.

In the modulation of cell cycle regulation of supportive cells by switching off the cell cycle inhibitor p27$^{Kip1}$, it was possible to achieve cell divisions in vivo (WO 99/42088). However, differentiation to sensory hair cells has hitherto only been observed under in vitro conditions outside of a tissue context (White et al., 2006).

In an in vivo model with induced sensory hair cell loss, gene therapeutically induced transdifferentiation of supportive cells with the transcription factor Math1, essential for sensory hair cell differentiation, led to conversion of supportive cells into sensory hair cells, even with partial functional recovery of the organ function (Izumikawa et al., 2005; Kawamoto et al., 2003). However, reduction in the number of supportive cells resulted in functional limitations for the organ of Corti as normal functioning of the complex micromechanic in the transduction process is impossible without supportive cells.

On activation of endogenous progenitor stem cells residing in the organ or of exogenous administration of heterologous stem cells to the inner ear, promising results were obtained (Tateya et al., 2003; Naito et al., 2004; Martinez-Monedero et al., 2007a, b; Li et al., 2003). However, a targeted or functionally relevant transplantation of stem cells into the inner ear has hitherto not been realized.

Accordingly, it could be helpful to identify low-molecular-weight compounds which stimulate an endogenous regeneration of terminally differentiated cells in highly specialized organs, tissues and sensory epithelia in mammals in situ. In particular, it could be helpful if these compounds could allow restoration of hearing in mammals by de novo formation of sensory hair cells in the adult organ of Corti. It could also be helpful for the first time to treat the causes of inner ear hardness of hearing on the basis of a pharmaceutical having regeneration biological activity.

SUMMARY

We provide aminoalkyloxazole and aminoalkylthiazole-carboxylic acid amides of formulae (1) and (2)

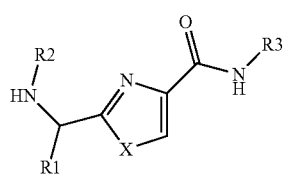

(1)

-continued

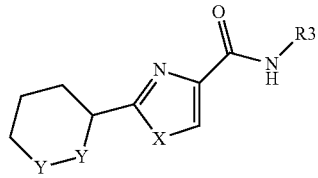

(2)

where X represents O or S, Y represents C or N, where the two atoms must be different from one another, R2 represents hydrogen or acyl and R1 and R3, which may be identical or different, represents a substituent selected from the group consisting of branched or straight-chain, substituted or unsubstituted alkyl groups, alkylcycloalkyl groups, alkylaryl groups, cycloalkyl groups, cycloalkylaryl groups, aryl groups and arylcycloalkyl groups which optionally contain heteroatoms, a pharmaceutically acceptable salt, a stereoisomer, a stereoisomer mixture, a tautomer or a prodrug compound, preferably a prodrug ester and a prodrug peptide, thereof.

BRIEF DESCRIPTION OF THE DRAWINGS

FIG. 1A shows cells from the inner ear can be obtained by individualizing the cells of the postnatal organ of Corti, isolating the stem cells still present and cultivating them under selective conditions in a suspension culture. Under these conditions, spheres are formed which express the stem cell marker Sox2 which is thought to have a decisive role in the pluripotency of embryonal stem cells and in the induction of pluripotent stem cells from differentiated cells (Takahashi and Yamanaka, 2006).

FIG. 1B shows the nuclei in the spheres incorporate BrdU which indicates the proliferation of the cells.

FIG. 1C shows expression of the household gene GAPDH as a standard.

FIG. 1D shows a stem cell marker which can also be detected during ontogenesis in the organ of Corti is expressed in the spheres. As positive control (pos), the mRNA from an organ of Corti of the embryonal development day 14.5 was applied. Standardized to the household gene GAPDH, it was possible to show that Jag1 is expressed both in the inner ear being formed and in the stem cells isolated therefrom.

FIG. 1E shows a stem cell marker which can also be detected during ontogenesis in the organ of Corti is expressed in the spheres. As positive control (pos), the mRNA from an organ of Corti of the embryonal development day 14.5 was applied. Standardized to the household gene GAPDH, it was possible to show that Nestin is expressed both in the inner ear being formed and in the stem cells isolated therefrom.

FIG. 1F shows a stem cell marker which can also be detected during ontogenesis in the organ of Corti is expressed in the spheres. As positive control (pos), the mRNA from an organ of Corti of the embryonal development day 14.5 was applied. Standardized to the household gene GAPDH, it was possible to show that Sox2 is expressed both in the inner ear being formed and in the stem cells isolated therefrom.

FIG. 1G shows a stem cell marker which can also be detected during ontogenesis in the organ of Corti is expressed in the spheres. As positive control (pos), the mRNA from an organ of Corti of the embryonal development day 14.5 was applied. Standardized to the household gene GAPDH, it was possible to show that Nanog is expressed both in the inner ear being formed and in the stem cells isolated therefrom.

FIG. 1H shows that, using optimized methods, it was possible to double the proportion of spheres formed from the primary culture compared to the currently published literature (Oshima et al., 2007; Senn et al., 2007).

FIG. 2E shows E-Cadherin labels all supportive cells orientated laterally to the pillar cells.

FIG. 2F shows E-Cadherin is also located in the membranes of the epithelial islands.

FIG. 2G shows that, in vivo, sensory hair cell markers, such as myosin VIIA reliably label inner and outer sensory hair cells.

FIG. 2H shows that myosin VIIA can also be detected in individual cells in the in vitro culture.

FIG. 2I shows that, in vivo, sensory hair cell markers, such as myosin VI, reliably label inner and outer sensory hair cells.

FIG. 2J shows that myosin VI can also be detected in individual cells in the in vitro culture.

FIG. 2K shows that, in vivo, sensory hair cell markers, such as calretinin, reliably label inner and outer sensory hair cells.

FIG. 2L shows that calretinin can also be detected in individual cells in the in vitro culture.

In the native organ, the asterisks in each case mark the 3 outer sensory hair cells and the inner sensory hair cell (always on the right-hand side).

Figure 2A:
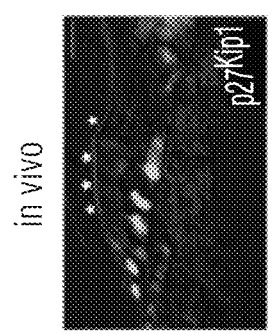
FIG. 2A shows $p27^{Kip1}$ is expressed in all supportive cells of the organ of Corti. Neither inner nor outer sensory hair cells are $p27^{Kip1}$-positive.
Figure 2B:
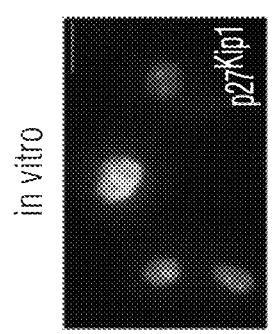
FIG. 2B shows it was possible to demonstrate $p27^{Kip1}$ expression within the epithelial islands.
Figure 2C:
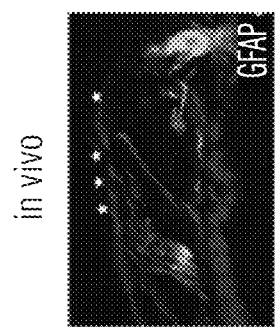
FIG. 2C shows GFAP labelling of supportive cells in the organ of Corti immediately below the nuclei of Deiter's cells and in the region of the inner phalangeal cells.
Figure 2D:
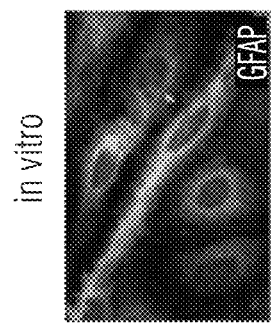
FIG. 2D shows the pattern of GFAP labelling of the filaments was also found in vitro.

Scale: 20 µm in the pictures of the naive organ of Corti FIGS. 2A, C, E, G, I and K, 10 µm in the cell culture FIGS. 2B, D, F, H, J and L.

Figure 3:
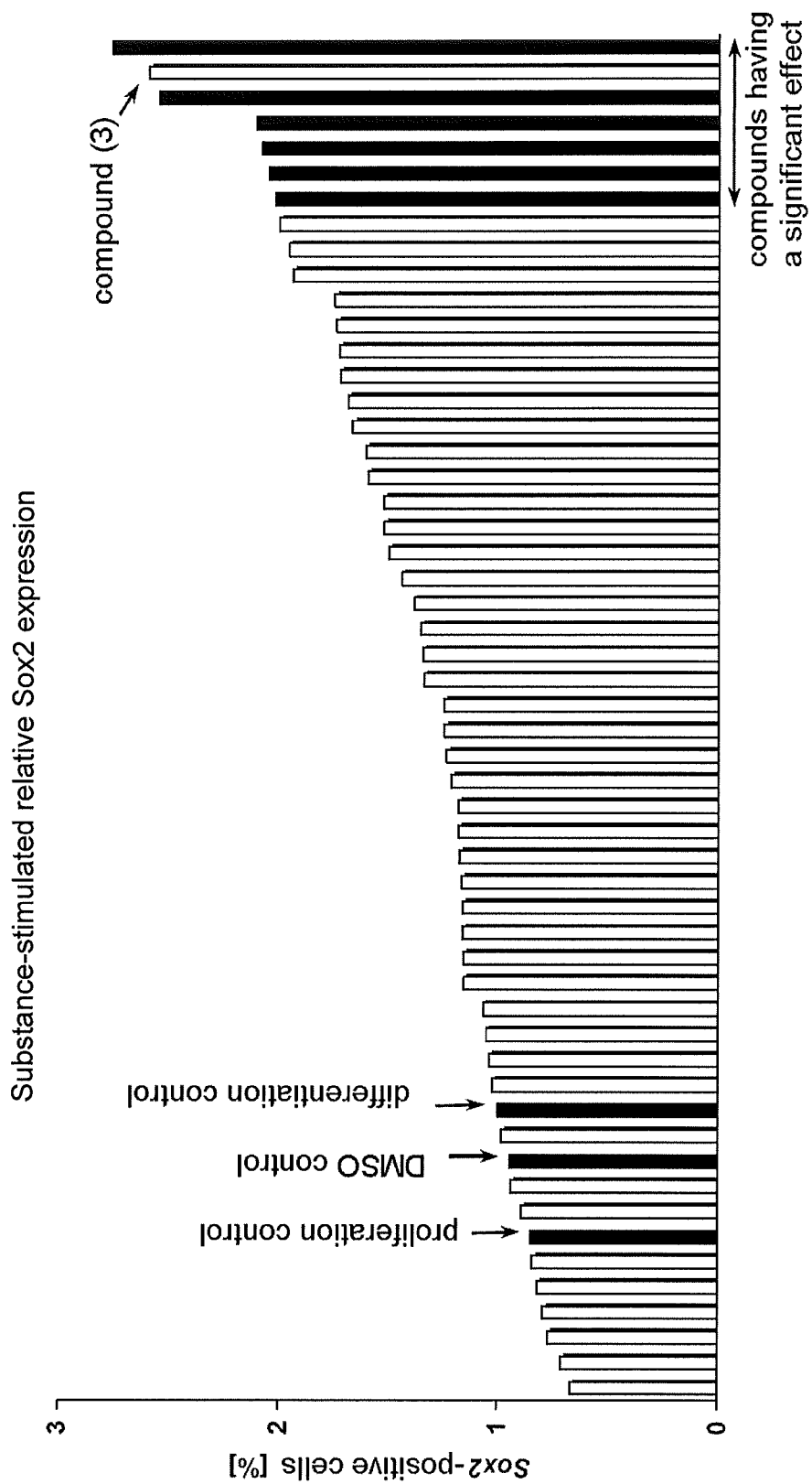

FIG. 3 shows relative number of cells expressing Sox2 in the screening assay.

It was examined which of the low-molecular-weight compounds were capable of inducing an increase in the proportion of Sox2-positive cells (as marker for the dedifferentiation of cells, standardized to the level of the differentiation control).

Seven compounds differ significantly from the control ($p<0.05$, $n=10$).

Figure 4:
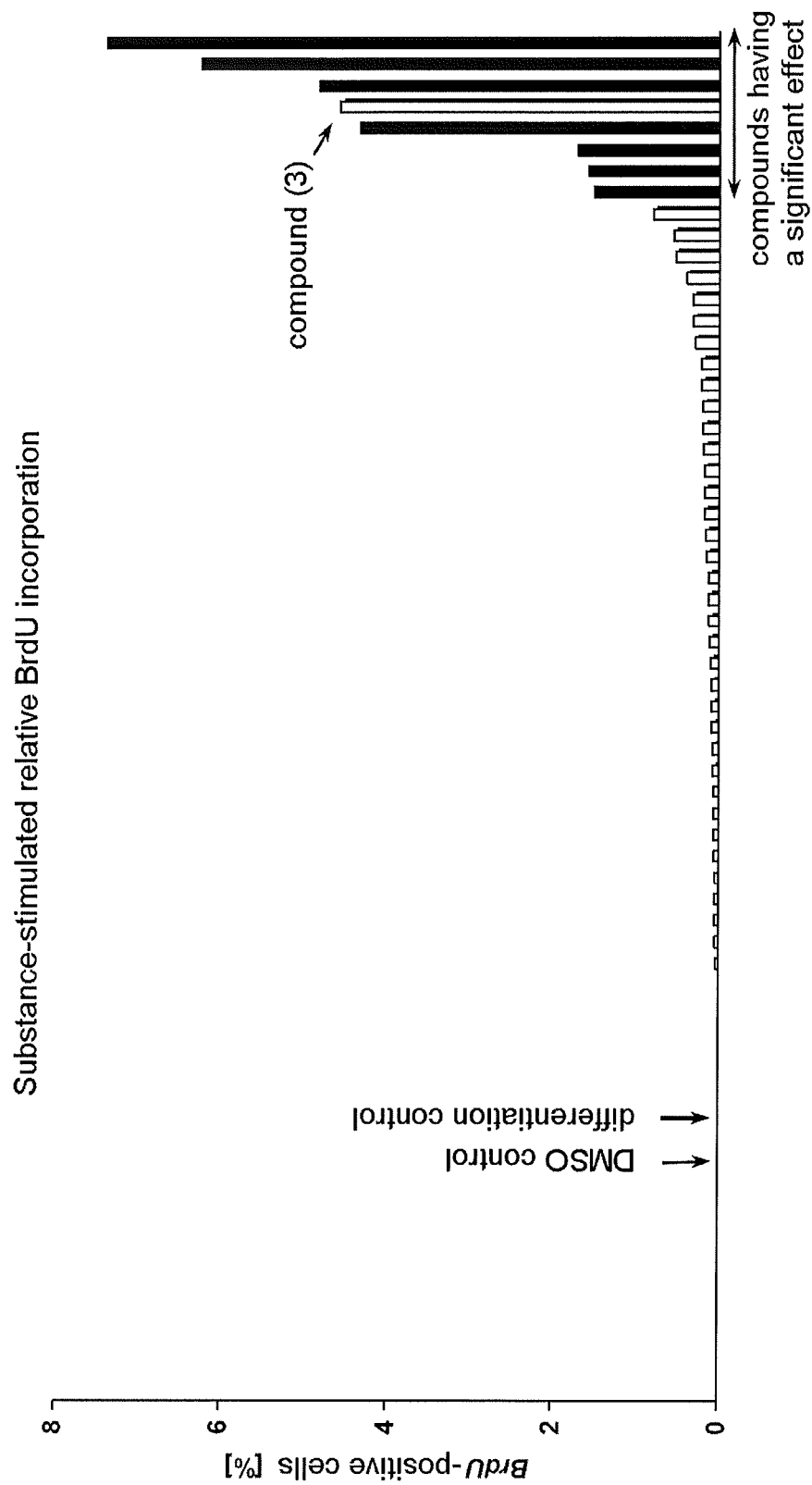

FIG. 4 shows relative number of BrdU-positive cells in the screening assay.

By detection of BrdU, it is possible to quantify how many cells have entered the S phase of the cell cycle within a certain period.

During screening, the cells were incubated with BrdU for five hours.

What is shown is the proportion of cells in the total population stimulated to proliferate by substance administration.

Eights compounds were able to induce significant proliferation ($p<0.05$, $n=10$).

Figure 5:
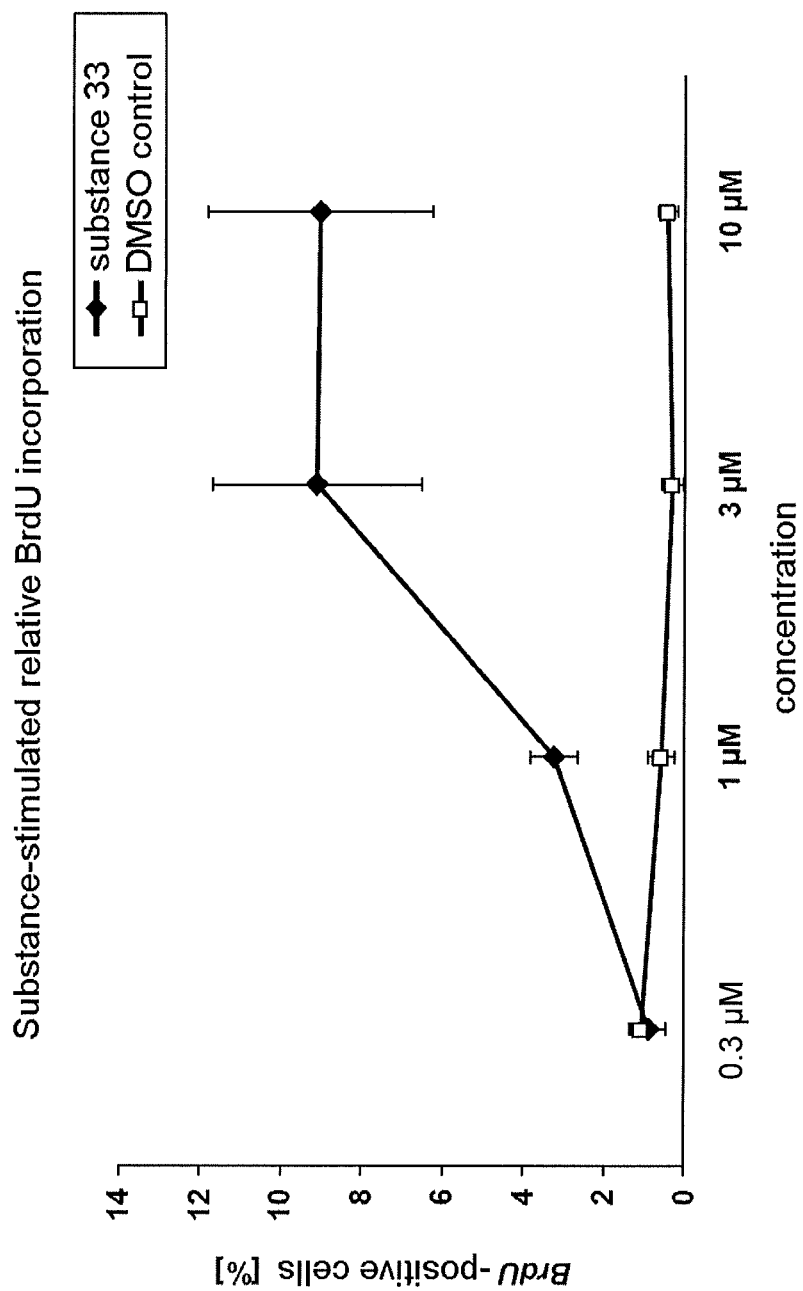

FIG. 5 shows dose/activity analysis for N-cyclohexyl-2-[1-amino-2-(1H-indol-3-yl)ethyl]oxazole-4-carboxylic acid amide (3) (substance 33).

In the adhesion culture, the dose-dependency of the induced BrdU effect was checked. When the substance concentration in the culture medium was increased from 0.3 µM to 3 µM, the BrdU incorporation increased to a significantly higher level ($p<0.05$, $n=10$). At higher concentrations, the BrdU incorporation could not be increased any further. The control, a population of cells from the in vitro culture with a comparable amount of DMSO without substance administration did not mediate any effect.

FIGS. 6A-6F show incorporation of BrdU induced by N-cyclohexyl-2-[1-amino-2-(1H-indol-3-yl)ethyl]oxazole-4-carboxylic acid amide (3) (substance 33) in the organ culture model.

The extent of the induced proliferation of supportive cells was demonstrated by incorporation of BrdU.

Figure 6C:
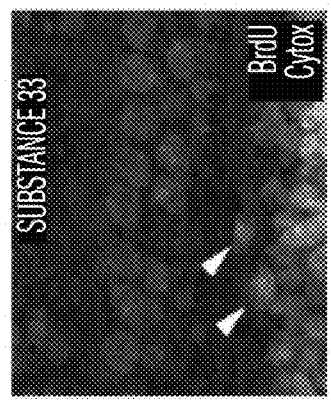
Figure 6B:
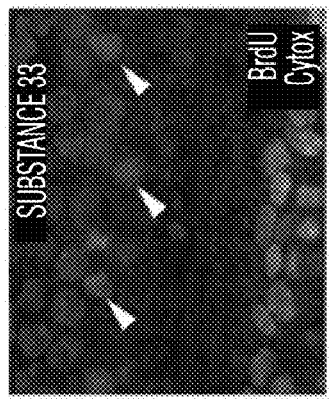
Figure 6A:

FIG. 6A shows in the control without substance administration, no incorporation of BrdU was observed in the Deiter's cells, the inner phalangeal cells and the border cells, FIG. 6B shows after administration of the compound (3) (substance 33, 5 µM), BrdU was incorporated into laterally orientated Deiter's cells.

FIG. 6C shows that after administration of substance 33, 5 µM, BrdU was incorporated into individual inner phalangeal cells and inner border cells.

Figure 6F:
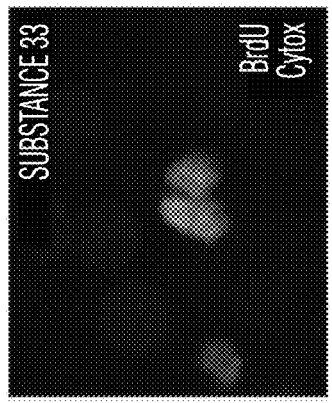
Figure 6E:
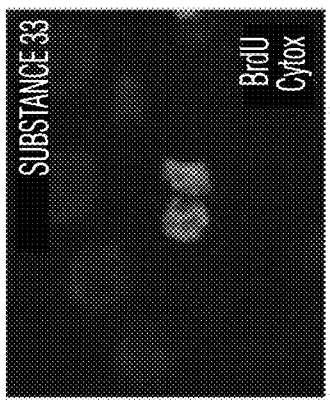
Figure 6D:
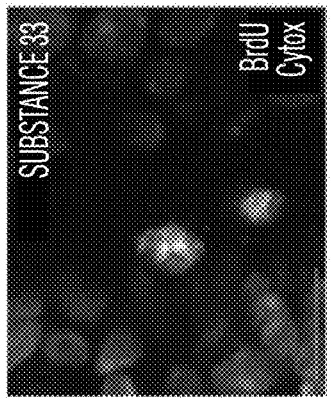

FIG. 6D shows the BrdU-positive nuclei at different stages of mitosis or had completed cell division.

Scale: 20 µm.

FIG. 6E shows the BrdU-positive nuclei at different stages of mitosis or had completed cell division.

Scale: 20 µm.

FIG. 6F shows the BrdU-positive nuclei at different stages of mitosis or had completed cell division.

Scale: 20 µm.

Figure 7C:
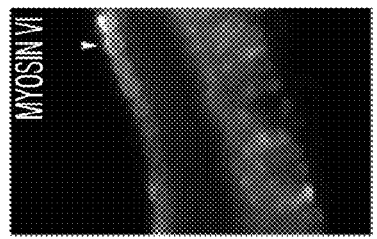
Figure 7E:
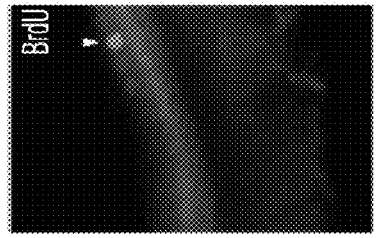
Figure 7B:
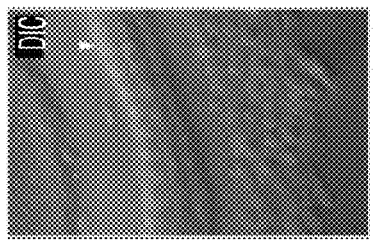
Figure 7D:
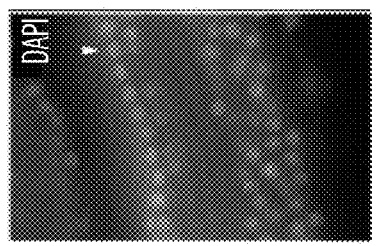
Figure 7A:
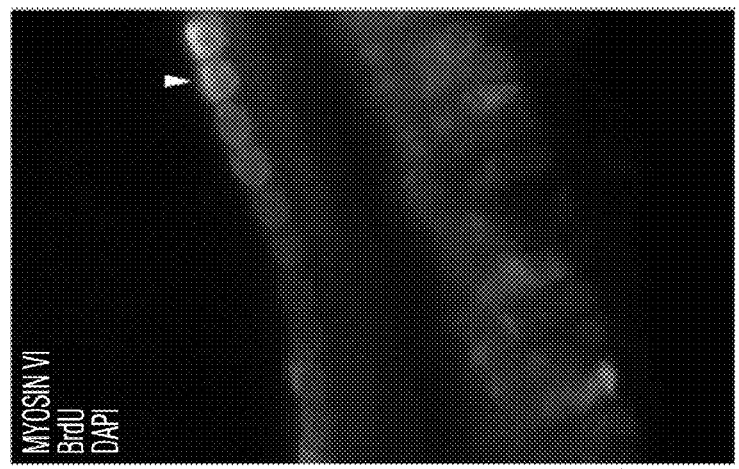

FIG. 7A shows triple labelling after intracochlear administration of N-cyclohexyl-2-[1-amino-2-(1H-indol-3-yl)ethyl]oxazole-4-carboxylic acid amide (3) in vivo.

In the in vivo experiment with adult guinea pigs, the regenerative effect of the compounds was demonstrated under reality-like conditions (administration over a period of 6 weeks using an Alzet® pump (200 µM) in parallel with BrdU (100 mg/ml), removal of the organ and staining after 8.5 weeks).

FIG. 7B shows inner sensory hair cells labelled with Sox2.

FIG. 7C shows inner sensory hair cells labelled with myosin VI (marker for sensory hair cells).

FIG. 7D shows inner sensory hair cells labelled with DAPI. The cell nucleus is labelled with DAPI (nucleus staining).

FIG. 7E shows inner sensory hair cells labelled with BrdU (marker for cell division).

Labelling with BrdU shows regeneration based on cell division.

DETAILED DESCRIPTION

We provide, for the first time, structurally defined chemically active compounds which can effect regeneration of terminally differentiated cells in mammals, in particular of sensory hair cells in the mammalian inner ear. For this reason, we provide novel, hitherto unknown low-molecular-weight compounds capable of stimulating regeneration biologically relevant processes such as dedifferentiation, proliferation and the resulting regeneration of cells from normally postmitotic tissues.

We furthermore provide for utilization of regeneration-promoting properties of the compounds for causal treatment of inner ear hardness of hearing after damage and loss of the sensory hair cells in the organ of Corti up to complete recovery of hearing in humans and animals.

Our low-molecular-weight compounds are able to induce corresponding cell biological changes such as dedifferentiation, proliferation and the subsequent terminal redifferentiation of cells of the normally post-mitotic tissue.

Due to the complex tissue structure in the inner ear, from among the various methods of regenerative medicine, only endogenous regeneration appears to be feasible as regeneration in situ. A precondition of the induction of this regeneration of the sensory hair cells is the suitable stimulation of the normally highly differentiated postmitotic auditory sensory epithelium. Target cells are the supportive cells, which are directly adjacent to the damaged cells and which may serve as potential precursors for a reformation of sensory hair cells.

Although, based on the current state of the art, it can be assumed that the regeneration biological mechanism of the dedifferentiation of cells can be triggered by certain active compounds, attempts to identify corresponding compounds for regeneration in the inner ear have hitherto been unsuccessful.

The ability of organic compounds to trigger a regeneration biologically relevant effect in the inner ear is target structure-dependent and impossible to predict accurately.

In addition to potentially active structural features, a decisive factor for the prospect of success in the biological tests is the selection of a suitable scaffold having active compound potential depending on and with reference to the target system.

By extensive screening of compounds with potential regeneration-promoting properties from various compound classes, we discovered that it is surprisingly possible to identify low-molecular-weight compounds capable of inducing, in vitro and in vivo, corresponding cell biological changes such as dedifferentiation and subsequent proliferation of otic supportive cells up to the regeneration of sensory hair cells. Using lead structure optimization, it was possible to develop structural analogs of these compounds having superior regeneration-promoting activity in mammals.

Accordingly, we provide to aminoalkyloxazole and aminoalkylthiazolecarboxylic acid amides of the formulae (1) and (2)

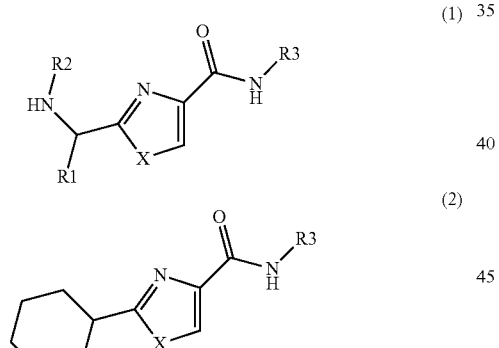

and to their use as active compounds for stimulating the endogenous in situ regeneration of terminally differentiated cells in highly specialized organs and tissues, preferably the brain, the heart, the skeletal muscles and particularly preferably sensory epithelia.

X represents O or S,

Y represents C or N, where the two atoms must be different from one another,

R2 represents hydrogen or acyl and

R1 and R3, which may be identical or different, represent a substituent selected from the groups below: branched or straight-chain, substituted or unsubstituted alkyl groups, alkylcycloalkyl groups, alkylaryl groups, cycloalkyl groups, cycloalkylaryl groups, aryl groups and arylcycloalkyl groups which optionally contain heteroatoms, where R1 preferably represents (1H-indol-3-yl)ethyl and R3 preferably represents cyclohexyl.

Preferably, the aminoalkyloxazole and aminoalkylthiazolecarboxylic acid amides correspond to the formulae (3) to (8) below.

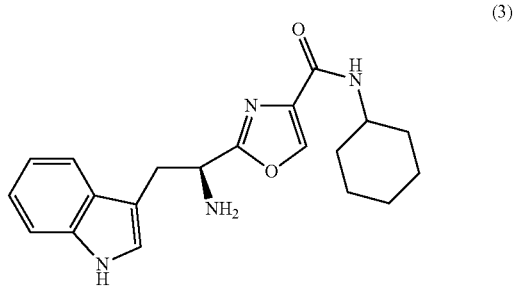

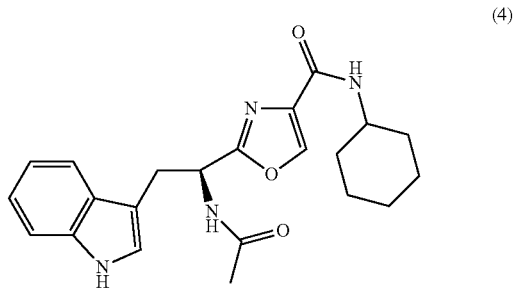

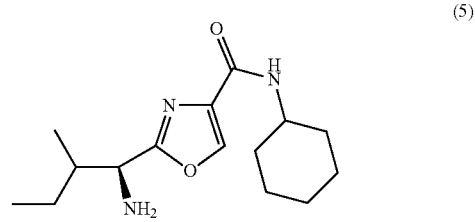

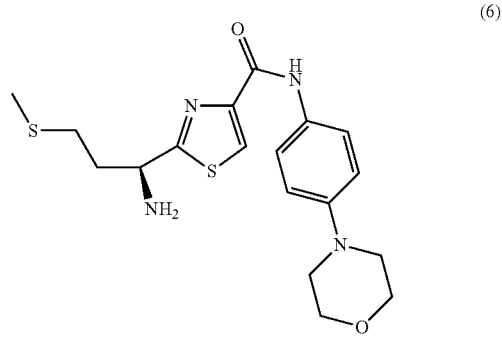

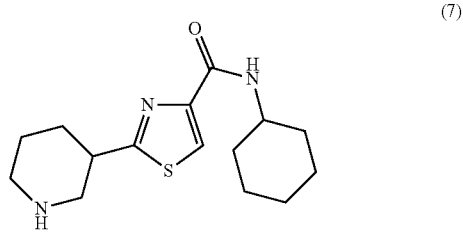

-continued

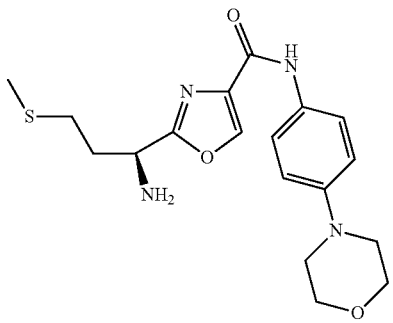

(8)

These definitions include pharmaceutically acceptable salts (preferably non-toxic and physiologically tolerated salts), the stereoisomers, stereoisomer mixtures, all tautomers, prodrug compounds, preferably prodrug esters or prodrug peptides, and mixtures of the compounds of the formulae (1) to (8).

The potential of the low-molecular-weight aminoalkyloxazole and aminoalkylthiazolecarboxylic acid amides for dedifferentiating cells which are already differentiated was demonstrated in a cell culture assay using stem cells, isolated from the inner ear of mice, which have otic development potential and, in cell culture, were differentiated to epithelium islands relatively similar to the original sensory epithelium. Compared to the control, the proportion of Sox2-expressing cells, a stem cell marker which is also expressed during ontogenesis of the organ of Corti and which is accepted as an indicator of cellular dedifferentiation, could be more than doubled by administration of the compounds. With a proportion of up to 7.4% BrdU (bromodeoxyuridine)-positive cells, as indicator of cellular proliferation, the activity of the compounds differs significantly from that of the differentiation and DMSO controls where no BrdU is incorporated.

It was thus possible to demonstrate the surprising biological activity of the compounds in the sense of the stimulation of dedifferentiation and subsequent proliferation of differentiated otic cells in an in vitro model.

Immunocytochemical analysis of the stem cell markers on the dedifferentiated epithelium confirmed the assumption that the compounds, after accumulation in the nucleus, first induce dedifferentiation of differentiated cells in the sense of reprogramming and then facilitate their proliferation.

In the cell culture model, by dose/activity analysis of the compounds, the concentration range for effective activity with regard to proliferation was defined to be in the range of from 0.1 μM to 100 μM, preferably from 1 μM to 3 μM, of substance in the cell culture medium.

Effects comparable to that in the cell culture assay were also achieved in the in vitro organ culture of a native organ of the mouse, i.e., in the complex cellular structure of the organ of Corti. After ototoxic damage of the sensory hair cells by the aminoglycoside antibiotic neomycin, administration of the compounds resulted in in situ proliferation of various supportive cells in the organ of Corti such as the laterally orientated Deiter's cells (outer phalangeal cells) and outer border cells in the region of the outer hair cells, the inner phalangeal cells and inner border cells in the region of the inner hair cells and also other supportive cells thought to be potential precursor cells for the regeneration of inner sensory hair cells. In detail, it was possible to demonstrate individual labelled nuclei in various stages of mitosis including completed cell division with two nuclei present.

In the in vivo model of the adult guinea pig, immunohistochemical findings additionally indicated regeneration, induced by the compounds of sensory hair cells based on cell divisions of supportive cells, preferably in the regions of the organ of Corti damaged by acoustic traumata. In corresponding control animals and control organs without administration of the compounds, no spontaneously regenerated hair cells were found.

In the in vitro and in vivo tests carried out to date, toxic effects or incompatibilities of the compounds have not been observed at the relevant concentration ranges.

We furthermore provide for preparation of the aminoalkyloxazole and aminoalkylthiazolecarboxylic acid amides which can be employed as active compounds for stimulating endogenous in situ regeneration of terminally differentiated cells in highly specialized organs and tissues, preferably the brain, the heart, the skeletal muscles and particularly preferably sensory epithelia.

Synthesis of the compounds is carried out in a number of steps. Detailed synthesis procedures can be found in Working Example A. The starting materials for preparing the compounds are known and can be obtained from the specialist trade or be prepared by known procedures.

One possible route is the synthesis of the compounds on a solid phase starting with an amino acid amide. To this end, the amino acid, the side chain of which represents substituent R1, is immobilized on a polymeric support having an activated carbonic ester group, and its acid group is then amidated. The cyclization of the amino acid amide to the oxazole or of the amino acid thioamide to the thiazole is carried out using bromopyruvic acid and N,N-dimethylaniline. If ethyl bromopyruvate is employed, the ester group formed has to be hydrolyzed afterwards. For the synthesis of the thiazoles, the amino acid amides are converted prior to the cyclization into the corresponding thioamides using Lawesson's reagent. The amino acid oxazole/thiazolecarboxylic acids obtained are then reacted with an amine representing the substituent R3. Finally, the amino acid oxazole/thiazolecarboxylic acid amides are cleaved with acid from the synthesis resin, followed by chromatographic purification.

In a further preparation variant, the synthesis of the compounds is carried out in solution. The synthesis takes place using protective group chemistry starting with a Boc-protected amino acid having the side chain R1. In principle, the steps of the synthesis correspond to those described for the solid phase. At the end of the synthesis, the Boc protective group is removed with acid, followed by chromatographic purification.

Both preparation processes permit the synthesis both of racemic and of enantiomerically pure compounds. The compounds are obtained either in free form or as a salt, provided salt-forming groups are present. Preferred salts of the compounds are pharmaceutically acceptable salts. Examples of such salts are salts of inorganic or organic acids, salts of inorganic or organic bases and salts of basic or acidic amino acids.

The compounds can also be modified as prodrug compounds, preferably as prodrug esters or prodrug peptides, or the like. In certain cases, by coupling cell penetration-enhancing molecules such as, for example, biotin or maleimidopropionic acid, optionally via suitable spacer molecules, to the primary amino group, or by acylation of this amino group, corresponding to substituent R2, it is possible to improve the bioavailability and thus the efficacy of the compounds.

We furthermore provide for use of the aminoalkyloxazole and aminoalkylthiazolecarboxylic acid amides to prepare pharmaceutical preparations for treating disorders in mammals associated with damaged postmitotic tissues, in particular for treating inner ear hardness of hearing in mammals caused by damage and loss of sensory hair cells in the organ of Corti. These preparations, comprising at least one active compound alone or in combination, optionally comprise further pharmaceutically suitable auxiliaries and additives such as, for example, carrier substances, preservatives, stabilizers, emulsifiers, detergents, solvents, solubilizers, salts for regulating the osmotic pressure and buffer salts. In addition, they may comprise further therapeutically relevant active compounds, adjuvants and also regeneration-promoting substances such as, for example, growth factors or anti-inflammatory agents.

Pharmaceutically suitable materials are the compounds known to be suitable for use in the field of pharmacy and food technology and related fields, in particular those listed in relevant pharmacopeias, whose properties do not exclude them from physiological administration.

The effects caused by the compounds also depend on their formulation. Appropriate pharmaceutical preparations should allow direct administration of the pharmaceutical into the cochlea of the mammal. Suitable administration forms of the pharmaceutical preparations comprising at least one active compound of formula (1) or (2) can be, for example, solutions, suspensions, sprays, gels, hydrogels, lotions, emulsions, pastes, ointments or creams.

The pharmaceutical preparations are prepared in a customary manner by known processes as described in relevant pharmacopeias, for example, by mixing, granulation or layering methods. The pharmaceutical preparations may additionally be sterilized.

We also provide for the use of the aminoalkyloxazole and aminoalkylthiazolecarboxylic acid amides as regeneration-promoting active compounds for treating, in humans and animals, disorders associated with damaged postmitotic tissues, preferably for recovery of hearing after loss or damage of sensory hair cells in the inner ear. To this end, a person or an animal in need of such a treatment is administered a therapeutically effective amount of a regeneration-promoting preparation comprising at least one compound of the formula (1) or (2). The active compound or the pharmaceutical preparation is applied directly or indirectly (including systemically), preferably locally, directly to/onto the damaged tissue structures. Administration onto or into the inner ear takes place, for example, transtympanally by injection into the middle ear, by application onto the round or oval window of the inner ear or by injection into the inner ear. Various systems for active compound administration (gel formulations, pumps) may be employed.

The compounds and pharmaceutical preparations may be employed on their own, in combination with other of our compounds or in combination with one or more active compounds relevant for the respective therapeutic indication described of the compounds. There are no restrictions with regard to the sequence of administration. Our compounds may be administered simultaneously with, before or after the other active compounds, as a separate pharmaceutical or as a combination preparation, and by the same or by different administration routes.

The exact therapeutically effective amount for the treatment of inner ear hardness of hearing in a subject depends on various factors, inter alia on the extent of the tissue damage, on the height, stature, age and state of health of the patient, on the administration route and the administration form, the compound actually employed and, if appropriate, other pharmaceuticals used. Thus, at the current point in time, it is not expedient to specify the exact amount. In principle, however, repeated administration of the pharmaceutical preparations over a period of up to 8 weeks at intervals of from one to seven days to continuous administration using "sustained release" systems provided with a mechanism for the metered sustained release of active compounds may be assumed. The amount of active compound employed should be in the range of from 0.5 μg to 1.0 mg per inner ear and administration.

Regeneration biologically relevant compounds capable of inducing corresponding cell biological changes such as dedifferentiation, proliferation or terminal redifferentiation and their formulations represent a novel form of active compounds since the therapeutic concept is completely new.

Using the aminoalkyloxazole and aminoalkylthiazolecarboxylic acid amides, it was possible, for the first time, to demonstrate cell division of otic supportive cells induced by low-molecular-weight compounds, and the resulting regeneration of sensory hair cells in the highly differentiated postmitotic tissue of the organ of Corti in mammals. Comparable methods for the in vivo regeneration of sensory hair cells based on pharmaceutically active compounds have hitherto not been described.

By virtue of the observed activity profiles of the compounds, these compounds are suitable for use as pharmaceutically active compounds for the causal therapeutic treatment of sensorineural hearing loss on a regeneration biological basis. In principle, this therapeutic approach is superior to all other methods discussed to date, such as gene therapy or stem cell transplantation. In the in vitro and in vivo models examined to date, no negative effects were observed.

More details on particularly preferred examples and further features and advantages are evident from the following description of working examples where the individual features mentioned above and still to be illustrated below are in each case claimed per se and in any combinations with one another.

The examples are purely for illustration and do not limit the scope of this disclosure.

EXAMPLES

Example A

Synthesis of 2-[1-aminoalkyl]oxazole-4-carboxylic acid amides and the corresponding 2-[1-aminoalkyl]thiazole-4-carboxylic acid amides The synthesis of the compounds was carried out starting with the amino acid amides making use of relevant publications for preparing similar compounds (Videnov et al., 1996; Stanchev et al., 1999; Stankova et al., 1999; Kaiser et al; 2000).

Both the intermediates and the end products were examined for purity and identity by HPLC and mass spectrometry. In addition, the end products were characterized by NMR spectroscopy. All starting materials and reagents are commercially available.

What is described herein below is a synthesis route on a solid polymer phase, starting with an amino acid amide. Since a great part of the synthetic procedures are identical, no separate synthesis processes were used for oxazoles and thiazoles. At the outset, the synthesis of tryptophanamide (11) as starting material for the particularly preferred compounds (3) and (4) is shown in an exemplary manner.

An alternative synthesis route in solution was then described for the thiazoles only. However, for one skilled in the art, it is not difficult to adapt the synthesis conditions to the oxazoles.

In the descriptions of the experiments, the abbreviations X, R1 and R3, which have the same meanings as in the patent claims, were used for the variable substituents.

The syntheses described allow the preparation of the compounds in stereochemically pure form. They are obtained either in free form or as a salt, provided salt-forming groups are present.

Preparation of D-Tryptophanamide (11)

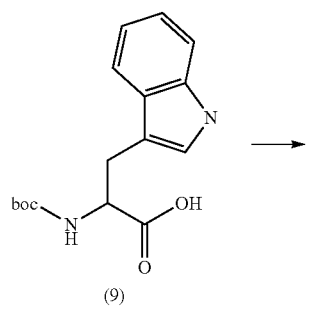

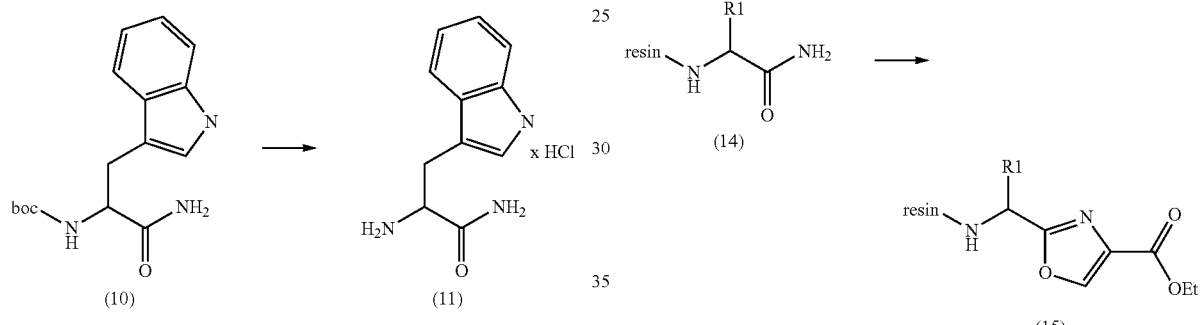

N-Boc-D-Tryptophan (9) (1 equiv.; 2.75 mmol; 1.00 g), hydroxybenzotriazole ammonium salt (2 equiv.; 5.50 mmol; 924 mg) and diisopropylcarbodiimide (DIC) (1.1 equiv.; 3.03 mmol; 382 mg; 454 µl) were dissolved in dimethylformamide (DMF) which had been dried over molecular sieves, and the solution was stirred at room temperature for 18 h. The solvent was then removed on a rotary evaporator under reduced pressure, and the residue was taken up in ethyl acetate. Insoluble residues were filtered off, and the organic phase was then washed (1×1 M KHSO₄ solution, 2× saturated aqueous sodium carbonate solution, 1× saturated aqueous sodium chloride solution), dried over sodium sulfate and evaporated.

To remove the Boc protective group, the crude product (10) was taken up in a solution of 50% trifluoroacetic acid (TFA) in dichloromethane (DCM) and stirred at room temperature for 3 h. After evaporation of the solvents, product (11) was recrystallized.

Loading of Chloro-(2'-Chloro)Trityl Polystyrene Resin (12) with Amino Acid Amide (13)

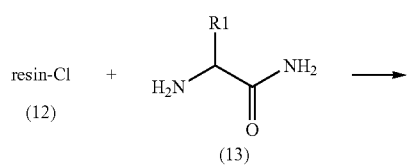

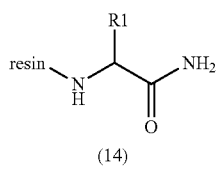

Chloro-(2'-chloro)trityl polystyrene resin (12) (Rapp Polymere H10033; loading 1.31 mmol/g) (1 equiv.; 655 mol; 500 mg) was washed twice with DMF (over molecular sieve), a solution of the amino acid amide hydrochloride (13) (2 equiv.; 1.31 mmol) and diisopropylethylamine (DIPEA) (5 equiv.; 3.28 mmol; 424 mg) in DMF was added and the mixture was shaken at room temperature for 18 h. To cap the resin, methanol (MeOH) was then added to the suspension and the mixture was shaken at room temperature for another 15 min. The reaction solution was filtered off with suction, the loaded resin (14) was washed (5×DMF, 3× each MeOH, tetrahydrofuran (THF), diethyl ether) and dried under oil pump vacuum.

Cyclization of the Immobilized Amino Acid Amide (14) to the Oxazole (15)

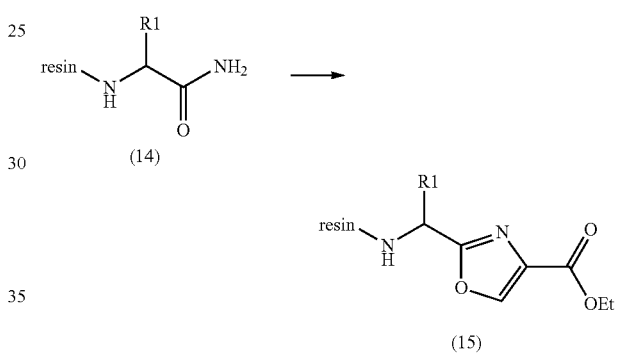

Ethyl bromopyruvate (5 equiv.; 3.28 mmol; 640 mg; 412 µl) and N,N-dimethylaniline (10 equiv.; 6.55 mmol; 794 mg; 832 µl) were dissolved in dioxane (5 ml) and added to the amino acid amide resin (14) (1 equiv.; 655 µmol; 500 mg). The suspension was shaken at room temperature for 16 h and then warmed at 60° C. for 2 h. The reaction solution was filtered off with suction and the resin was washed with dry solvents (5×DMF, 5×DCM).

A solution, cooled to −20° C., of pyridine (10 equiv.; 6.55 mmol; 520 mg; 530 µl) in dry DCM (5 ml) was mixed with trifluoroacetic anhydride (5 equiv.; 3.28 mmol; 688 mg; 456 µl) and added to the washed resin. After 30 min at −20° C., the suspension was warmed to room temperature and shaken at room temperature for a further 2 h. The reaction solution was filtered off with suction and the resin (15) was washed (3× each DMF, MeOH, THF, DCM, diethyl ether) and dried under reduced pressure in a desiccator.

Preparation of Immobilized Thioamides (16) with Lawesson's Reagent

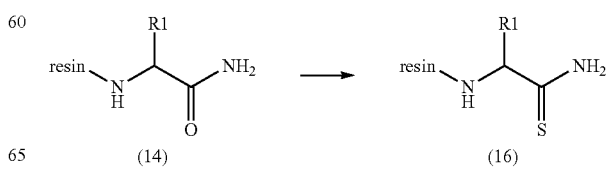

A solution of Lawesson's reagent (3 equiv.; 1.97 mmol; 797 mg) in dimethoxyethane (DME) (10 ml) was added to the amino acid amide resin (14) (1 equiv.; 655 µmol; 500 mg), and the mixture was shaken at room temperature for 18 h. The reaction solution was filtered off with suction and the resin (16) was washed (6×DMF, 3× each MeOH, THF, DCM, diethyl ether) and dried under reduced pressure in a desiccator.

Cyclization of the Immobilized Thioamide (16) to Thiazole (17)

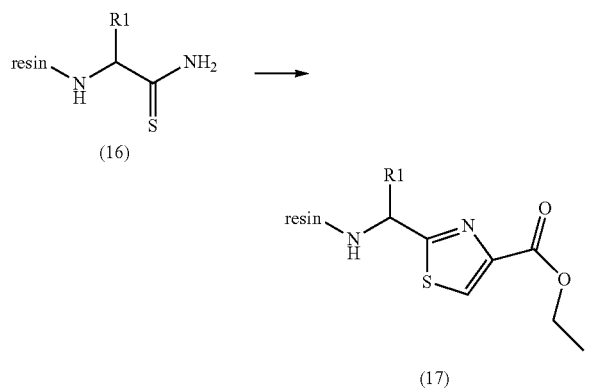

Ethyl bromopyruvate (5 equiv.; 3.28 mmol; 640 mg; 412 µl) and N,N-dimethylaniline (5 equiv.; 3.28 mmol; 397 mg; 416 µl) were dissolved in DMF (4 ml) and added to the amino acid thioamide resin (16) (1 equiv.; 655 µmol; 500 mg). The suspension was shaken at room temperature for 16 h. The reaction solution was filtered off with suction and the resin (17) was washed (3× each DMF, MeOH, THF, DCM, diethyl ether) and dried under reduced pressure in a desiccator.

After a test cleavage using 5% TFA in DCM at room temperature for 1 h, identity and purity of reaction product (17) were checked by chromatography and mass spectrometry.

Hydrolysis of the Immobilized Ethyl Esters (15) and (17)

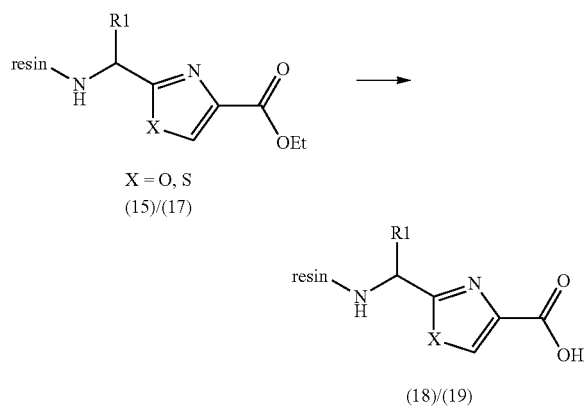

The amino acid oxazolecarboxylic acid ethyl ester resin (15) or amino acid thiazolecarboxylic acid ethyl ester resin (17) (1 equiv.; 655 µmmol; 500 mg) was pre-swollen in THF (2.5 ml), and a solution of lithium hydroxide monohydrate (5 equiv.; 3.28 mmol; 137 mg) in water (1.25 ml) and MeOH (1.25 ml) was added. After 3 h at room temperature, the reaction solution was filtered off with suction, the resin (18) or (19) was washed (3× each water, water/DMF 1:1, DMF, dioxane, THF, DCM, diethyl ether) and dried under reduced pressure in a desiccator.

Amidation of the Carboxylic Acids (18) and (19) and Cleavage from the Resin

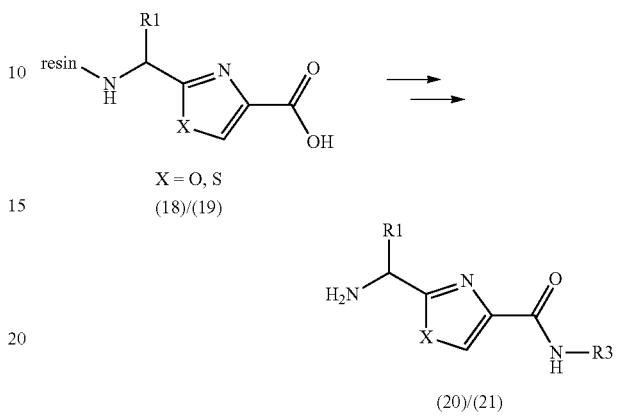

A solution of 1-hydroxybenzotriazole (HOBt) (5 equiv.; 3.28 mmol; 443 mg) and DIC (5 equiv.; 3.28 mmol; 413 mg) in dry DMF (5 ml) was added to the amino acid oxazolecarboxylic acid resin (18) or amino acid thiazolecarboxylic acid resin (19) (1 equiv.; 655 µmol; 500 mg). After 30 min of shaking at room temperature, the R3-amine (10 equiv.; 6.55 mmol) was added and the suspension was shaken at room temperature for a further 16 h. The reaction solution was filtered off with suction and the resin was then washed (3× each DMF, MeOH, THF, DCM, diethyl ether) and sucked dry in a stream of air.

The product (20) or (21) was then cleaved from the resin at room temperature using a solution of 5% TFA in DCM for 1 h.

After evaporation of the cleavage solutions, the crude product was lyophilized from tBuOH/water 4:1 and chromatographed on silica gel using a DCM/MeOH gradient.

Preparation of the Thioamides (23) with Lawesson's Reagent in Solution

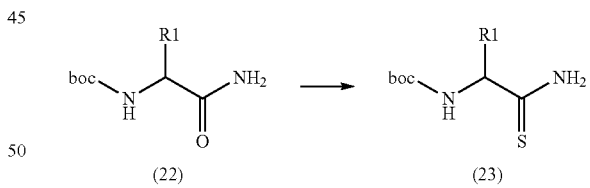

With stirring, Lawesson's reagent (0.75 equiv.; 750 mol; 305 mg) was added to a solution of the Boc-amino acid amide (22) (1 equiv.; 1.00 mmol) in dry DME (7.5 ml). The reaction solution was stirred at room temperature for 16 h and the solvent was then removed by distillation on a rotary evaporator under reduced pressure. The residue was taken up in ethyl acetate (30 ml) and stirred vigorously with 10% strength sodium bicarbonate solution (15 ml) for 30 min. After separation of the phases, the aqueous phase was extracted twice with ethyl acetate. The combined organic phases were washed three times with 10% strength sodium bicarbonate solution and then dried over sodium sulfate. After filtration, the solvent was distilled off and the product (23) was dried under oil pump vacuum.

The crude products can be recrystallized from ethyl acetate or ethyl acetate/petroleum ether or purified by flash chromatography on silica gel.

Cyclization of Thioamides (23) to Thiazole (24) in Solution

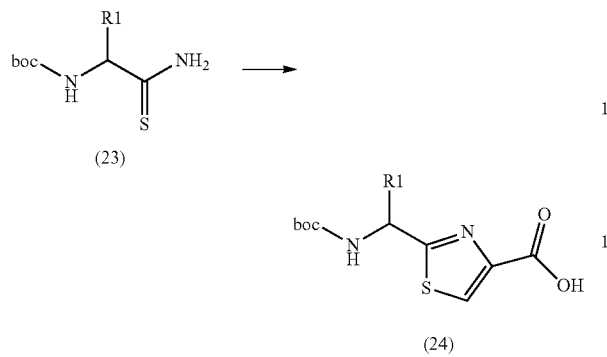

Calcium carbonate (2 equiv.; 1.60 mmol; 161 mg) was added to a solution of the Boc-amino acid thioamide (23) (1 equiv.; 0.80 mmol) in anhydrous ethanol (6 ml), and the suspension was stirred at room temperature for 10 min. Bromopyruvic acid (1.5 equiv.; 1.20 mmol; 201 mg) was then added. After 4 h of stirring at room temperature, the reaction mixture was filtered and the residue was washed with ethanol. The combined filtrates were concentrated on a rotary evaporator under reduced pressure, and the residue was taken up in ethyl acetate (10 ml) and extracted three times with 10 ml of 5% strength potassium bisulfate solution and once with saturated sodium chloride solution. The organic phase was then dried over sodium sulfate. After filtration, the solvent was distilled off and the product (24) was dried under oil pump vacuum.

The crude products were purified by flash chromatography on silica gel.

Amidation of Thiazole (24) and Removal of the Boc Protective Group in Solution

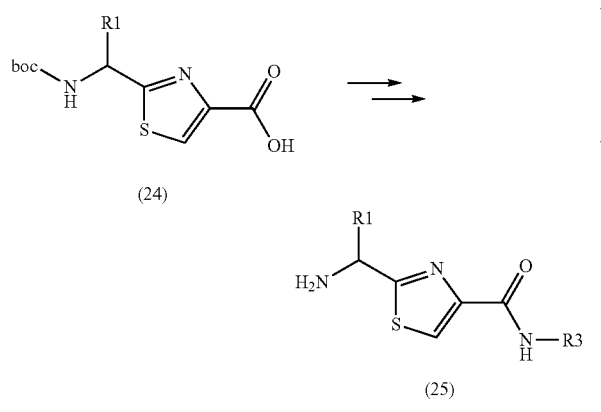

(Benzotriazol-1-yloxy)tripyrrolidinophosphonium hexafluorophosphate (PyBOP) (1.05 equiv.; 0.84 mmol; 437 mg) and triethylamine (TEA) (3 equiv.; 2.40 mmol; 242 mg; 330 µl) were added to the Boc-amino acid thiazolecarboxylic acid (24) (1 equiv.; 0.80 mmol) in THF, and the mixture was stirred at room temperature for 30 min. The R3-amine (1.3 equiv.; 1.04 mmol) was then added, and the mixture was stirred at room temperature for 18 h.

The reaction solution was evaporated and the crude product was chromatographed on silica gel using a DCM/MeOH gradient.

To remove the Boc protective group, the amide was stirred in 25% TFA in DCM at room temperature for 1 h and then evaporated. Repeatedly, heptane was added to the crude product and removed by distillation again on a rotary evaporator under reduced pressure. The product (25) was then lyophilized from tBuOH/water 4:1.

N-Acetylation of N-cyclohexyl-2-[1-amino-2-(1H-indol-3-yl)ethyl]oxazole-4-carboxylic acid amide (3)

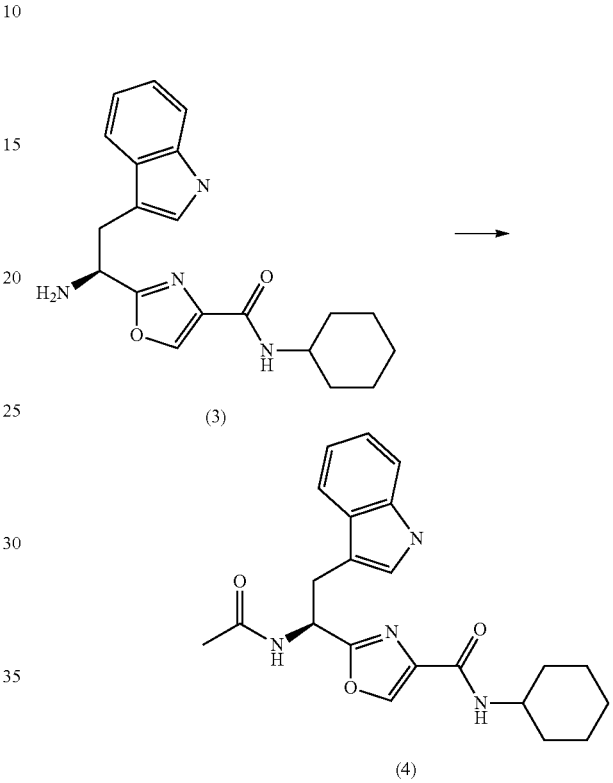

Acetic anhydride (5 equiv.; 140 µmol; 14 mg; 13 µl) and TEA (2 equiv.; 56 µmol; 6 mg; 8 µl) were added to the aminoalkyloxazolecarboxylic acid amide (3) (1 equiv.; 28 µmol; 10 mg) in DCM (0.5 ml), and the mixture was stirred at room temperature for 18 h. The reaction solution was then evaporated and the crude product (4) was lyophilized from tBuOH/water 4:1.

Example B

Demonstration of the Regenerative Properties in the In Vitro Cell Culture Assay

First, starting with stem cells with otic development potential isolated from the postnatal organ of Corti of the mouse, typical cellular cluster "spheres" were grown in a suspension culture. Under culture conditions optimized compared to known processes (Oshima et al., 2007; Senn et al., 2007) in a DMEM/F12 medium (Dulbecco's Modified Eagle Medium) supplemented with B27 and N2, about 1600 solid spheres per organ of Corti could be generated from the stem cell culture with added FGF (fibroblast growth factor) and IGF (insulin-like growth factor) (FIG. 1H).

By labelling on the protein level (FIGS. 1A and 1B) and demonstrating a plurality of stem cell markers on the mRNA level (FIG. 1C to FIG. 1G), it was shown that the otospheres formed under these culture conditions are in a dedifferentiated state which corresponds to an earlier state during ontogenesis in the organ of Corti. In addition, it was possible to demonstrate cell divisions in the otospheres.

In situ, supportive cells are the potential precursors for a regeneration of sensory hair cells and therefore the actual target cells for the induction of sensory hair cell regeneration. For this purpose, it was necessary to establish in vitro a joint culture of hair- and supportive cell-like cells constituting a relatively good representation of the cellular composition of the organ of Corti.

To this end, the cultivated otospheres were differentiated in a second step under adherent culture conditions on an ornithine/fibronectin surface to give monolayer epithelium islands relatively similar to the original sensory epithelium.

By immunocytochemical detection, it was possible to identify, on the protein level, in each case three suitable markers for supportive cells and sensory hair cells. FIGS. 2A to 2L show a comparison of the situation in the native organ (in vivo) and in the differentiated epithelium islands of the cell culture (in vitro) using these markers.

These preliminary studies carried out by prior art methods and without addition of our compounds showed that the cultivated otic epithelium islands are suitable as a cellular base for demonstrating the regenerative potential of the compounds for supportive cell-like cells of the inner ear. Changes of the protein expression of markers for supportive cells, hair cells and stem cells can be use to demonstrate the effects mediated by the substances administered.

For screening, firstly the proportion of Sox2-positive cells in the in vitro culture was determined. Sox2 is a stem cell marker, which is also expressed during ontogenesis of the organ of Corti. It is thought to have an important role in the pluripotency of embryonal stem cells and during induction of pluripotent stem cells from differentiated cells (Takahashi and Yamanaka, 2006). Accordingly, Sox2 is an important marker, in particular in the context of an induced dedifferentiation/reprogramming of cells.

By adding our compound N-cyclohexyl-2-[1-amino-2-(1H-indol-3-yl)ethyl]oxazole-4-carboxylic acid amide (3) to the cell culture, the proportion of Sox2-expressing cells could be more than doubled compared with the differentiation control (FIG. 3).

If the expression of stem cell markers induced by the compounds is in the end also associated with an increased proliferation of the cells in culture was checked by quantification of the BrdU-positive cells. During substance administration the culture was incubated for 5 h with the thymidine analog BrdU. During the S phase of the cell cycle, cell division results in incorporation of BrdU. If one of the substances stimulates cell division, this can be detected and visualized with an antibody directed against BrdU.

By adding our compound N-cyclohexyl-2-[1-amino-2-(1H-indol-3-yl)ethyl]oxazole-4-carboxylic acid amide (3) to the cell culture, it was possible to induce proliferation in 4.8% of the cells differentiated beforehand (FIG. 4).

Both with regard to Sox2 expression and BrdU incorporation, our compound 2-[1-amino-2-(1H-indol-3-yl)ethyl]oxazole-4-carboxylic acid N-cyclohexylamide (3) achieved significant positive results. In this manner, it was shown that the compound is capable of inducing dedifferentiation and subsequent proliferation of otic supportive cells.

In a dose/activity analysis, the optimum concentration range in which this compound unfolds its maximum regeneration biological effect in the cell culture was determined.

To this end, incorporation of BrdU in the stem cell-based in vitro cell culture assay was determined at 4 concentrations between 0.3 µM and 10 µM in the culture medium. It was found that with the concentration of 0.3 µM, no significant effect was achieved. However, at a concentration of 1 µM, the mean was already elevated. From a concentration of 3 µM, the saturation level of about 9% BrdU-positive cells is already reached (FIG. 5).

Example C

Demonstration of the Regenerative Properties in the In Vitro Organ Culture Model To confirm the effects observed in the cell culture assay in the native organ, i.e., in situ in the complex cellular structure of the organ of Corti, use was made of a form of organ culture where the tissue to be cultivated, in the present case the entire inner ear of the mouse, was located in a rotating cylinder filled with culture medium (Hahn et al., 2008). Before the start of the experiment, the cochlea was opened basally and apically in the region of the scala tympani. In this manner, it was possible to minimize the effect of gravity and at the same time to achieve optimum gas and nutrient exchange between the tissue of the organ of Corti and the culture medium. Under these conditions, the explantate could be kept in culture for longer compared to a stationary culture.

To demonstrate that, as a result of the administration of the compounds, the supportive cells remaining in the organ of Corti after loss of sensory hair cells dedifferentiate to precursor cells and then proliferate, a situation analogous to a hard of hearing ear was established. After administration of the ototoxic aminoglycoside antibiotic neomycin (1 mM), ⅔ of all sensory hair cells suffered cell death within 24 hours. Only in the apical regions of the cochlea, some sensory hair cells survived, the number of which declined further during the course of the experiment as a result of the initial damage. After removal of the neomycin from the medium, the remaining supportive cells could be cultivated further.

BrdU was then added to the culture medium simultaneously with the compounds (5 µM), and after 4 days the proliferation was quantified by BrdU incorporation.

After addition of the compound N-cyclohexyl-2-[1-amino-2-(1H-indol-3-yl)ethyl]oxazole-4-carboxylic acid amide (3) to the organ culture, BrdU incorporation could be demonstrated in the furthest laterally orientated Deiter's cells (FIG. 6B). This was also the case for individual inner phalangeal cells and border cells (FIG. 6C) which are associated with the inner sensory hair cell and can be considered to be potential precursor cells for their regeneration. In control experiments without substance administration, there was no spontaneous incorporation of BrdU into Deiter's cells, inner phalangeal cells and inner border cells (FIG. 6A).

The different morphology of the BrdU-positive nuclei indicated various stages of mitosis up to completed cell division. Chromatin condensation could be observed in various nuclei (FIGS. 6D, E). At the same time, BrdU-positive nuclei were found in immediate relative proximity of one another (FIGS. 6E, F).

This means that, due to the action of the compound N-cyclohexyl-2-[1-amino-2-(1H-indol-3-yl)ethyl]oxazole-4-carboxylic acid amide (3), new cells in the sense of a regeneration by cell division of supportive cells have been formed in the sensory epithelium of the organ of Corti.

Example D

Demonstration of Regenerative Properties after In Vivo Administration

The regeneration biological effect of the compounds was likewise demonstrated in the in vivo model of the adult guinea pig. Acute acoustic damage resulting in a loss of sensory hair cells of the organ of Corti, in particular in the region of the outer sensory hair cells, was caused by impulse noise. The compound N-cyclohexyl-2-[1-amino-2-(1H-indol-3-yl)ethyl]α-azole-4-carboxylic acid amide (3) was then continuously administered locally from a miniosmotic pump (Alzet®), subcutaneously implanted, via choleostomy directly into the scala tympani of the cochlea. The dosage of the substance in the pump was correspondingly higher at 200 µM, taking into account an expected dilution effect in the perilymph.

Administration was over a period of 6 weeks, with a subsequent waiting interval of 2 weeks. In parallel, BrdU was administered via the drinking water or the miniosmotic pump to label proliferating cells in the organ of Corti.

After removal of the organ of Corti, immunohistochemical triple labelling with BrdU (cell division), myosin VI (sensory hair cells) and DAPI (staining of the nuclei) FIGS. 7A to 7E and also with Sox2 (pluripotent supportive cells) was carried out.

BrdU-labelled supportive cells and sensory hair cells were preferably demonstrated in the regions of the organ of Corti damaged by acoustic trauma. In control organs of the opposite side with/without acoustic damage and without substance administration, no BrdU-labelled sensory hair cells and, altogether, in accordance with the known findings on spontaneous proliferation, only few BrdU-labelled cells were found.

The in vivo findings show unambiguously that regeneration of sensory hair cells on the basis of cell divisions can be induced even in the adult animal by administration of the compound N-cyclohexyl-2-[1-amino-2-(1H-indol-3-yl)ethyl]oxazole-4-carboxylic acid amide (3). This underlines the surprisingly great potential of the compounds as active compounds for the causal treatment of inner ear hardness of hearing by regeneration of sensory hair cells.

Example E

Toxicity

In the cell culture, organ culture and in vivo studies, no indications of toxic effects of the aminoalkyloxazole and aminoalkylthiazolecarboxylic acid amides were found in the concentration range examined from 0.3 µM to 200 µM.

LITERATURE

1. Chen S, Zhang Q, Wu X, Schultz P G, Ding S (2004) Dedifferentiation of lineage-committed cells by a small molecule. J Am Chem Soc 126(2):410-411
2. Corwin J T, Cotanche D A (1988) Regeneration of sensory hair cells after acoustic trauma. Science 240:1772-1774
3. Cotanche D A (1987) Regeneration of hair cell stereocilia bundles in the chick cochlea following severe acoustic trauma. Hear Res 30:181-196
4. Cotanche D A (1999) Structural recovery from sound and aminoglycoside damage in the avian cochlea. Audiol Neurootol 4:271-285
5. Cruz R M, Lambert P M, Rubel E W (1987) Light microscopic evidence of hair cell regeneration after gentamicin toxicity in chick cochlea. Arch Otolaryngol Head Neck Surg 113:1058-1062
6. Daudet N, Vago P, Ripoll C, Humbert G, Pujol R, Lenoir M (1998) Characterization of atypical cells in the juvenile rat organ of Corti after aminoglycoside ototoxicity. J Comp Neurol 401:145-162
7. Daudet N, Ripoll C, Lenoir M (2002) Transforming growth factor induced cellular changes in organotypic cultures of juvenile, amikacin-treated rat organ of Corti. J Comp Neurol 442:6-22
8. Feng B, Ng J H, Heng J C, Ng H H (2009) Molecules that promote or enhance reprogramming of somatic cells to induced pluripotent stem cells. Cell Stem Cell 4(4):301-312
9. Hahn H, Müller M, Lowenheim H (2008) Whole organ culture of the postnatal sensory inner ear in simulated microgravity. J Neurosci Meth 171(1):60-71
10. ifo-Institut far Wirtschaftsforschung in cooperation with Infratest Gesundheitsforschung on behalf of the German Green Cross, Marburg "Hörtest 1985", Section "Gutes Hören" (1986)
11. Izumikawa M, Minoda R, Kawamoto K, Abrashkin K A, Swiderski D L, Dolan D F, Brough D E, Raphael Y (2005) Auditory hair cell replacement and hearing improvement by Atohl gene therapy in deaf mammals. Nat Med 11:271-276
12. Kaiser D, Videnov G, Maichle-Mossmer C, Strahle J, Jung G (2000) X-ray structures and ab initio study of the conformational properties of novel oxazole and thiazole containing di- and tripeptide mimetics. J Chem Soc Perkin Trans 2:1081-1085
13. Kawamoto K, Ishimoto S I, Minoda R, Brough D E, Raphael Y (2003) Math1 gene transfer generates new cochlear hair cells in mature guinea pigs in vivo. J Neurosci 23:4395-4400
14. Kelley M W, Talreja D R, Corwin J T (1995) Replacement of hair cells after laser microbeam irradiation in cultured organs of Corti from embryonic and neonatal mice. J Neurosci 15:3013-3026
15. Kim S, Rosania G R, Chang Y T (2004) Dedifferentiation? What's next? Mol Intery 4:83-85
16. Li H, Liu H, Heller S (2003) Pluripotent stem cells from the adult mouse inner ear. Nat Med 9:1293-1299
17. Li W, Ding S (2009) Small molecules that modulate embryonic stem cell fate and somatic cell reprogramming. Trends Pharmacol Sci 31(1):36-45
18. Martinez-Monedero R, Edge A S (2007a) Stem cells for the replacement of inner ear neurons and hair cells. Int J Dev Biol 51:655-661
19. Martinez-Monedero R, Oshima K, Heller S, Edge A S (2007b) The potential role of endogenous stem cells in regeneration of the inner ear. Hear Res 227:48-52
20. McGann C J, Odelberg S J, Keating M T (2001) Mammalian myotube dedifferentiation induced by new regeneration extract. Proc Natl Acad Sci USA 98(24):13699-13704
21. Nadol J B Jr (1993) Hearing Loss. N Engl J Med 329:1092-1102
22. Naito Y, Nakamura T, Nakagawa T, Iguchi F, Endo T, Fujino K, Kim T S, Hiratsuka Y, Tamura T, Kanemaru S, Shimizu Y, Ito J (2004) Transplantation of bone marrow stromal cells into the cochlea of chinchillas. Neuroreport 15:1-4
23. Odelberg S J (2002) Inducing cellular dedifferentiation: a potential method for enhancing endogenous regeneration in mammals. Semin Cell Dev Biol 13(5):335-343
24. Oshima K, Grimm C M, Corrales C E, Senn P, Martinez-Monedero R, Geleoc G S, Edge A S, Holt J R, Heller S (2007) Differential distribution of stem cells in the auditory and vestibular organs of the inner ear. J Assoc Res Otolaryngol 8:18-31
25. Roberson D W, Rubel E W (1994) Cell division in the gerbil cochlea after acoustic trauma. Am J Otol 15:28-34

26. Ruben R J (1967) Development of the inner ear of the mouse. A autoradiographic study of terminal mitosis. Acta Otolaryngol (Stockh) [Suppl]220:1-44
27. Ryals B M, Rubel E W (1988) Hair cell regeneration after acoustic trauma in adult Coturnix Quail. Science 240: 1774-1776
28. Schugar R C, Robbins P D, Deasy B M (2008) Small molecules in stem cell self-renewal and differentiation. Gene Ther 15(2):126-135
29. Senn P, Oshima K, Teo D, Grimm C, Heller S (2007) Robust postmortem survival of murine vestibular and cochlear stem cells. J Assoc Res Otolaryngol 8(2):194-204
30. Smolders J W T (1999) Functional recovery in the avian ear after hair cell regeneration. Audiol Neurootol 4:286-302
31. Staecker H, Lefebvre P P, Malgrange B, Moonen G, Van De Water T R (1995) Technical comments: Regeneration and mammalian auditory hair cells. Science 267(5198): 709-711
32. Stanchev M, Tabakova S, Videnov G, Golovinsky E, Jung G (1999) Synthesis and antimicrobial activity in vitro of new amino acids and peptides containing thiazole and oxazole moieties. Arch Pharm 332:297-304
33. Stankova I G, Videnov G I, Golovinsky E V, Jung G (1999) Synthesis of thiazole, imidazole and oxazole containing amino acids for peptide backbone modification. J Peptide Sci 5:392-398
34. Takahashi K, Yamanaka S (2006) Induction of pluripotent stem cells from mouse embryonic and adult fibroblast cultures by defined factors. Cell 126(4):663-676
35. Tateya I, Nakagawa T, Iguchi F, Kim T S, Endo T, Yamada S, Kageyama R, Anito Y, Ito J (2003). Fate of neural stem cells grafted into injured inner ears of mice. Neuroreport 14:1677-1681
36. Tsonis P A (2000) Regeneration in vertebrates. Dev Biol 221(2):273-284
37. Tsonis P A (2002) Regenerative biology: the emerging field of tissue repair and restoration. Differentiation 70(8): 397-409
38. Tsonis P A (2004) Stem cells from differentiated cells. Mol Intery 4(2):81-83
39. Vago P, Humbert G, Lenoir M (1998) Amikacin intoxication induces apoptosis and cell proliferation in rat organ of Corti. Neuroreport 9:431-436
40. Videnov G, Kaiser D, Kempter, C, Jung G (1996) Synthesis of naturally occurring, conformationally restricted oxazole- and thiazole containing di- and tripeptide mimetics. Angew Chem Int Ed Eng135(13/14):1503-1506
41. White P M, Doetzlhofer A, Lee Y S, Groves A K, Segil N (2006) Mammalian cochlear supporting cells can divide and trans-differentiate into hair cells. Nature 441:984-987
42. Xu Y, Shi Y, Ding S (2008) A chemical approach to stem-cell biology and regenerative medicine. Nature 453 (7193):338-344
43. Yamasoba T, Kondo K, Miyajima C, Suzuki M (2003) Changes in cell proliferation in rat and guinea pig cochlea after aminoglycoside-induced damage. Neurosci Lett 347: 171-174
44. Yamasoba T, Kondo K (2006) Supporting cell proliferation after hair cell injury in mature guinea pig cochlea in vivo. Cell Tissue Res 325: 23-31

The invention claimed is:
1. A method of treating inner ear hardness of hearing and restoring hearing of humans and animals after damage and loss of sensory hair cells in an organ of Corti based on regeneration biology, comprising administering a therapeutically effective amount of a compound comprising aminoalkyloxazole and aminoalkylthiazole carboxylic acid amides of formula (1)

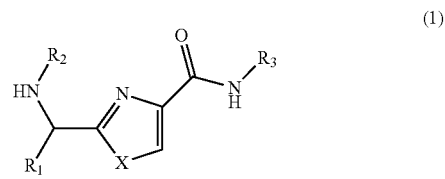

wherein
X represents oxygen (O) or sulfur (S),
$R_2$ represents hydrogen (H) or acyl,
$R_1$ represents branched or straight-chain, substituted or unsubstituted aryl groups or alkylaryl groups, which optionally contain heteroatoms, and
$R_3$ represents branched or straight-chain, substituted or unsubstituted alkyl groups, cycloalkyl groups or alkylcycloalkyl groups,
or
a pharmaceutically acceptable salt, a stereoisomer, a stereoisomer mixture, a tautomer or a prodrug compound thereof,
directly or indirectly to damaged tissue structures in a cochlea, optionally, by transtympanal injection into a middle ear, by application to a round or oval window of an inner ear or by injection into the inner ear.

2. The method as claimed in claim 1, wherein X represents O.

3. The method as claimed in claim 1, wherein $R_2$ represents H.

4. The method as claimed in claim 2, wherein $R_2$ represents H.

5. The method as claimed in claim 1, where $R_1$ represents (1H-Indol-3-yl)-ethyl.

6. The method as claimed in claim 1, wherein $R_3$ is a substituted or unsubstituted cycloalkyl group.

7. The method as claimed in claim 1, wherein
X represents O,
$R_2$ represents H,
$R_1$ represents (1H-Indol-3-yl)-ethyl, and
$R_3$ represents substituted or unsubstituted cycloalkyl.

8. The method as claimed in claim 1 having formula (3)

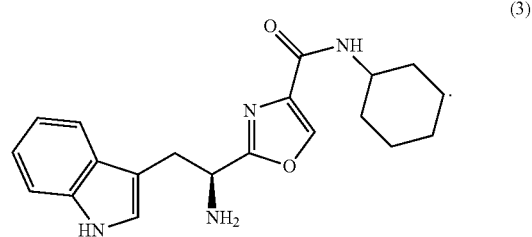 [SMILES: N[C@@H](Cc1c[nH]c2ccccc12)c1nc(C(=O)NC2CCCCC2)co1]

9. A method of treating inner ear hardness of hearing and restoring hearing of humans and animals after damage and loss of sensory hair cells in an organ of Corti based on regeneration biology, comprising administering a therapeutically effective amount of a pharmaceutical preparation comprising aminoalkyloxazole and aminoalkylthiazole carboxylic acid amides of formula (1)

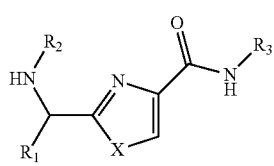

(1)

wherein
- X represents oxygen (O) or sulfur (S),
- $R_2$ represents hydrogen (H) or acyl,
- $R_1$ represents branched or straight-chain, substituted or unsubstituted aryl groups or alkylaryl groups, which optionally contain heteroatoms, and
- $R_3$ represents branched or straight-chain, substituted or unsubstituted alkyl groups, cycloalkyl groups or alkyl-cycloalkyl groups, or a pharmaceutically acceptable salt, a stereoisomer, a stereoisomer mixture, a tautomer or a prodrug compound thereof, directly or indirectly to damaged tissue structures in a cochlea, optionally, by transtympanal injection into a middle ear, by application to a round or oval window of an inner ear or by injection into the inner ear.

10. The method as claimed in claim 9, wherein the pharmaceutical preparation is in the form of a solution, suspension, spray, gel, hydrogel, lotion, emulsion, paste, ointment or cream.

* * * * *